United States Patent
Naito et al.

(10) Patent No.: US 8,821,388 B2
(45) Date of Patent: Sep. 2, 2014

(54) MULTIJOINTED BENDING MECHANISM AND MULTIJOINTED MEDICAL EQUIPMENT HAVING MULTIJOINTED BENDING MECHANISM

(75) Inventors: Kimihiko Naito, Hachioji (JP); Tsutomu Ishiguro, Hino (JP); Jun Hasegawa, Hino (JP); Toshio Nakamura, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1138 days.

(21) Appl. No.: 12/556,956

(22) Filed: Sep. 10, 2009

(65) Prior Publication Data

US 2009/0326325 A1   Dec. 31, 2009

Related U.S. Application Data

(63) Continuation of application No. PCT/JP2007/074240, filed on Dec. 17, 2007.

(30) Foreign Application Priority Data

Mar. 29, 2007   (JP) ................................. 2007-086483

(51) Int. Cl.
*A61B 1/00* (2006.01)
*A61B 1/005* (2006.01)
*A61B 19/00* (2006.01)
*A61B 17/29* (2006.01)
*A61B 17/00* (2006.01)

(52) U.S. Cl.
CPC ............... *A61B 1/0055* (2013.01); *A61B 19/22* (2013.01); *A61B 2017/2947* (2013.01); *A61B 2017/2929* (2013.01); *A61B 2017/2927* (2013.01); *A61B 2019/2276* (2013.01); *A61B 2017/2901* (2013.01); *A61B 2017/003* (2013.01); *A61B 2017/2908* (2013.01); *A61B 17/29* (2013.01); *A61B 2019/2242* (2013.01); *A61B 1/0057* (2013.01)

USPC .......................... 600/141; 600/146; 600/149

(58) Field of Classification Search
CPC .. A61B 1/005; A61B 1/00149; A61B 1/0051; A61B 1/0053; A61B 1/0055; A61B 1/0056; A61B 1/0057; A61B 1/008; A61B 1/01
USPC ......... 600/102, 139, 141, 144, 146, 149, 142, 600/145, 148, 150
See application file for complete search history.

(56) References Cited

U.S. PATENT DOCUMENTS

| | | | | |
|---|---|---|---|---|
| 4,686,963 | A | * | 8/1987 | Cohen et al. .................. 600/141 |
| 5,179,935 | A | * | 1/1993 | Miyagi ......................... 600/142 |
| 2002/0032371 | A1 | | 3/2002 | Torii |

FOREIGN PATENT DOCUMENTS

| | | |
|---|---|---|
| JP | 47-12398 | 4/1972 |
| JP | 4-170930 | 6/1992 |

(Continued)

OTHER PUBLICATIONS

European Search Report dated May 8, 2012 from corresponding European Patent Application No. EP 07 85 0728.2.

(Continued)

*Primary Examiner* — Alireza Nia
(74) *Attorney, Agent, or Firm* — Scully, Scott, Murphy & Presser, P.C.

(57) ABSTRACT

A multijointed bending mechanism having a first bending piece, a second bending piece connected to the first bending piece so as to be rotatable around a first rotation shaft, a third bending piece connected to the second bending piece so as to be rotatable around a second rotation shaft, at least two first wires connected to the first bending piece to rotate the first bending piece and at least two second wires connected to the second bending piece to rotate the second bending piece. The second wires are disposed inwards of the first wires with respect to a vertical direction of the first and second rotation shafts.

14 Claims, 12 Drawing Sheets

(56) References Cited

FOREIGN PATENT DOCUMENTS

| | | |
|---|---|---|
| JP | 6-105797 | 4/1994 |
| JP | 6-114000 | 4/1994 |
| JP | 2003-126024 | 5/2003 |
| JP | 2003-220022 | 8/2003 |
| JP | 2007-54400 | 3/2007 |

OTHER PUBLICATIONS

Official Action dated Jun. 25, 2010 received from the China Patent Office with English translation.

* cited by examiner

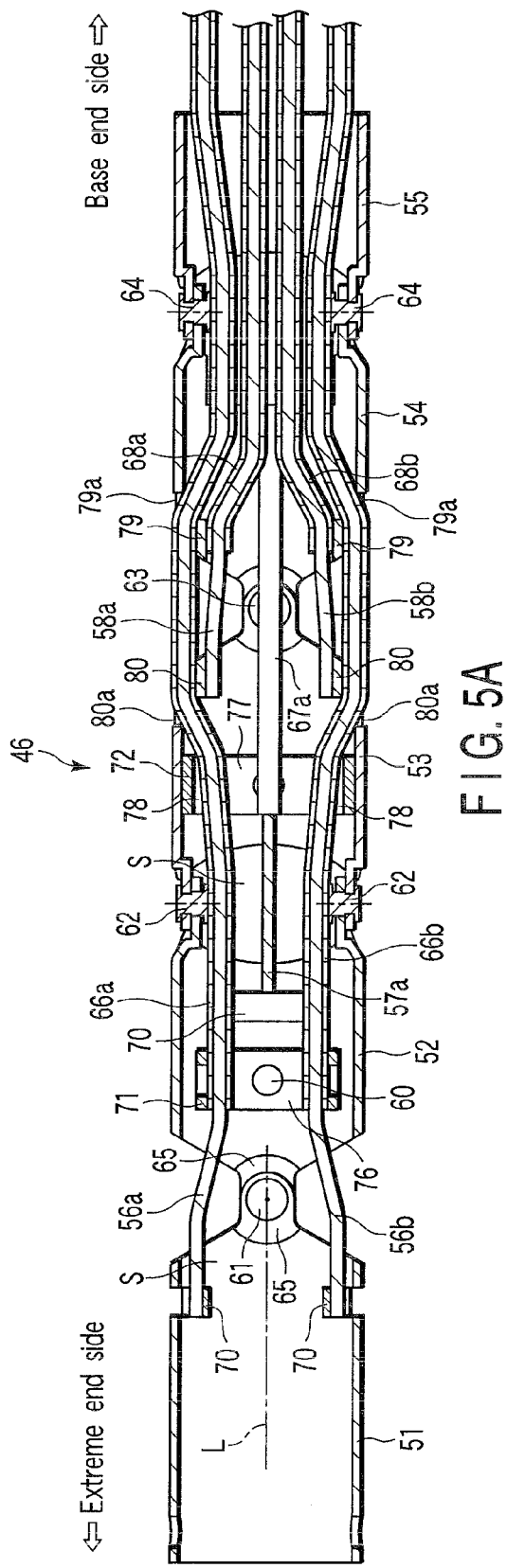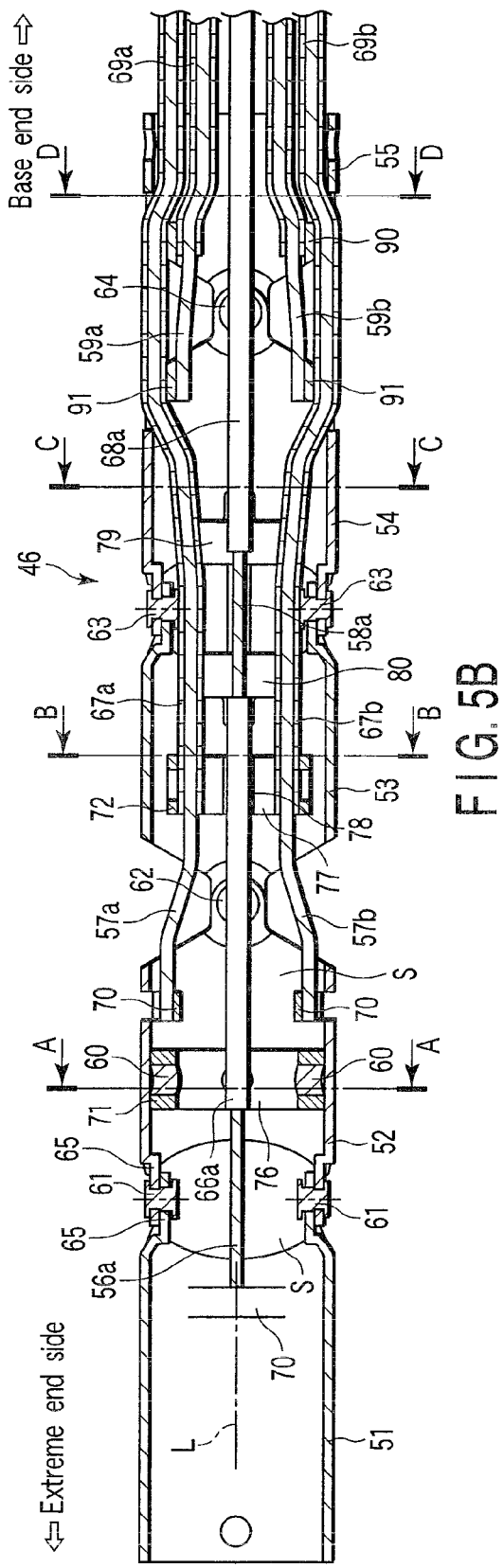

Cross section A-A

Cross section B-B

Cross section C-C

Cross section D-D

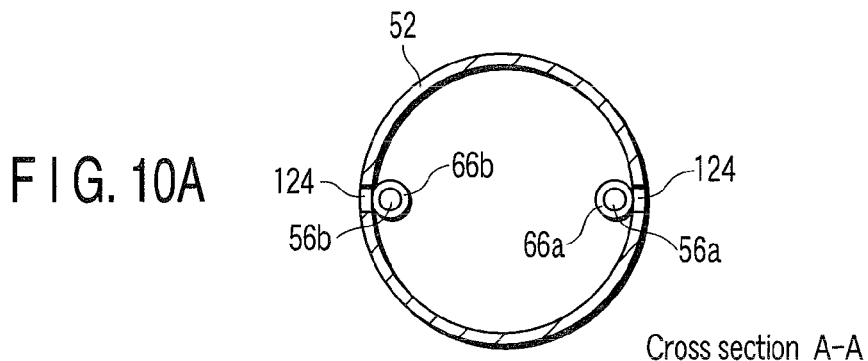
FIG. 10A  Cross section A-A
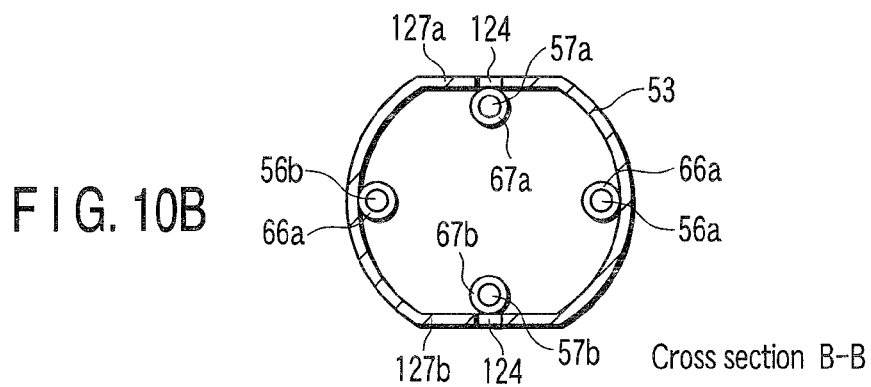
FIG. 10B  Cross section B-B
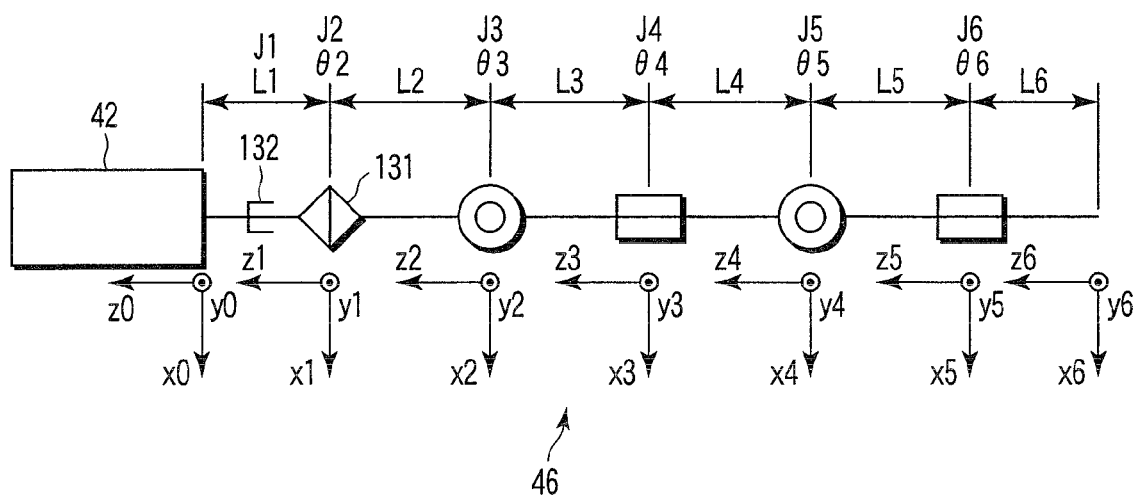
FIG. 11

US 8,821,388 B2

MULTIJOINTED BENDING MECHANISM AND MULTIJOINTED MEDICAL EQUIPMENT HAVING MULTIJOINTED BENDING MECHANISM

CROSS REFERENCE TO RELATED APPLICATIONS

This is a Continuation Application of PCT Application No. PCT/JP2007/074240, filed Dec. 17, 2007, which was published under PCT Article 21(2) in Japanese.

This application is based upon and claims the benefit of priority from prior Japanese Patent Application No. 2007-086483, filed Mar. 29, 2007, the entire contents of which are incorporated herein by reference.

BACKGROUND OF THE INVENTION

1. Field of the Invention

The present invention relates to a multijointed bending mechanism in which a plurality of bending pieces can be independently manipulated by manipulation wires, and to a multijointed medical equipment having such multijointed bending mechanism.

2. Description of the Related Art

In general, an insertion portion of a piece of medical equipment such as an endoscope is provided with a bending portion. Bending pieces are rotatably coupled with each other in the bending portion. A manipulation wire is connected only to a bending piece at the most extreme end of the bending portion. The bending portion is bent in its entirety by pushing and pulling the manipulation wire. More specifically, since the respective bending pieces cannot be independently rotated, it is difficult for the bending pieces to take a predetermined bending state.

To cope with the above problem, in Patent Document 1, repellent force application means is disposed in the base end portion of a bending portion. When the bending portion is bent by a manipulation wire, the repellent force application means begins to bend the bending portion preferentially from the extreme end portion thereof. Further, in Patent Document 2, balloons are interposed between bending pieces, respectively. Rotation intervals between bending pieces are adjusted by the expansion and contraction of the balloons. With this configuration, when a bending portion is bent, the radius of bending of the bending portion can be variably adjusted.

Patent Document 1: Jpn. Pat. Appln. KOKAI Publication No. 2003-126024

Patent Document 2: Jpn. Pat. Appln. KOKAI Publication No. 06-105797

BRIEF SUMMARY OF THE INVENTION

Accordingly, the present invention provides a multijointed bending mechanism in which only an arbitrary bending pieces can be independently rotated, a space in which a surgical instrument and the like are disposed can be secured, and manipulation wires can be disposed compactly without being entangled with each other and multijointed medical equipment having the multijointed bending mechanism.

According to an aspect of the present invention, there is provided a multijointed bending mechanism comprising: a first bending piece; a second bending piece connected to the first bending piece so as to be rotatable around a first rotation shaft; a third bending piece connected to the second bending piece so as to be rotatable around a second rotation shaft; at least two first wires connected to the first bending piece to rotate the first bending piece; and at least two second wires connected to the second bending piece to rotate the second bending piece, wherein the second wires are disposed inwards of the first wires with respect to a vertical direction of the first and second rotation shafts.

According to an aspect of the present invention, there is provided a multijointed bending mechanism comprising: a first bending piece; a second bending piece connected to the first bending piece so as to be rotatable around a first rotation shaft; a third bending piece connected to the second bending piece so as to be rotatable around a second rotation shaft; at least two first wires connected to the first bending piece to rotate the first bending piece; and at least two third wires connected to the third bending piece to rotate the third bending piece, wherein the third wires are disposed inwards of the first wires with respect to a vertical direction of the first and second rotation shafts.

An aspect of the present invention provides a multijointed medical equipment having the multijointed bending mechanism.

BRIEF DESCRIPTION OF THE SEVERAL VIEWS OF THE DRAWING

FIG. 5A is a horizontal longitudinal sectional view of the bending portion along line A-A in FIG. 4 in the long axis direction of the insertion portion, as viewed from above.

FIG. 5B is a vertical longitudinal sectional view of the bending portion along line B-B in FIG. 4 in the long axis direction of the insertion portion, as viewed from the left side thereof.

FIG. 10A shows a modification of the positioning/disposing mechanism and is a lateral sectional view along a line A-A in FIG. 5B.

FIG. 10B shows a modification of the positioning/disposing mechanism and is a lateral sectional view along a line B-B in FIG. 5B.

FIG. 11 is an explanatory view of a multijointed structure in a bending portion of a surgical instrument in still another embodiment of the present invention.

DETAILED DESCRIPTION OF THE INVENTION

A multijointed surgical instrument (for example, multijointed medical equipment) having a multijointed bending mechanism according to an embodiment of the present invention and an endoscope system having such multijointed surgical instrument will be explained below with reference to the drawings.

Figure 1:
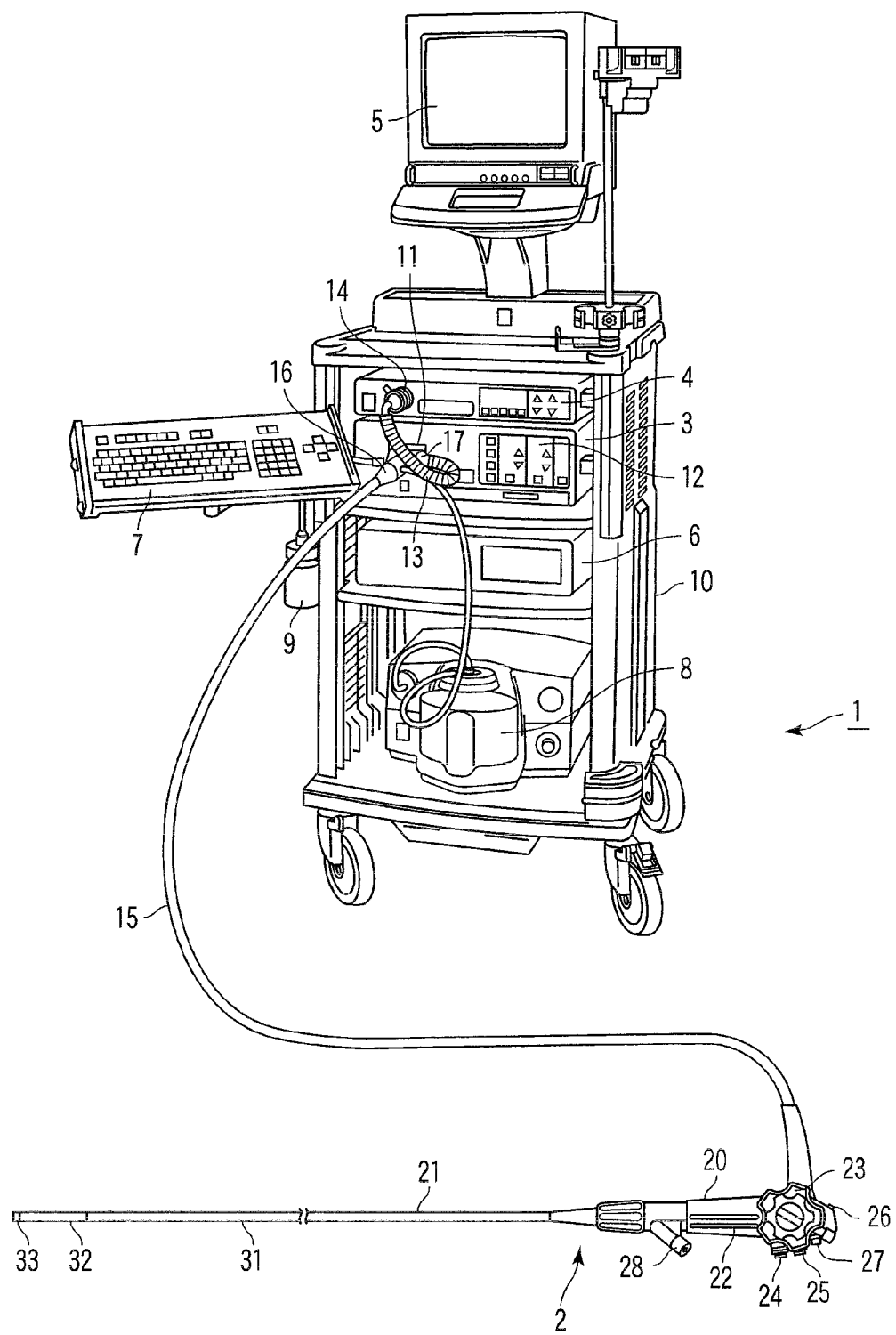
FIG. 1 is a perspective view schematically showing an endoscope apparatus included in an endoscope system according to an embodiment of the present invention.

FIG. 1 is a perspective view schematically showing an endoscope apparatus 1 included in the endoscope system. The endoscope apparatus 1 is composed of an electronic endoscope (endoscope main body) 2 and a peripheral device (device main body) of the endoscope 2.

The peripheral device includes a light source unit 3 for creating endoscope illumination light, an image processing unit 4 for subjecting an image picked up by an image pickup portion (not shown) in the endoscope 2 to various types of image processing, an image display unit (for example, monitor) 5 for displaying an image, image data (the image processed by the image processing unit 4), a state of the device, an instruction of an operator, and the like, a controller 6 for overall control of the endoscope system and executing an arithmetic operation and the like, an input unit 7 having a keyboard and the like, a waste fluid tank 8 with a suction pump, a water feed tank 9, and the like. The peripheral device is mounted on a trolley 10.

The light source unit 3 has a connection port 11 connected to a connector unit 16 and a display 12 for displaying an operating state of the light source unit 3 on the front surface thereof.

The image processing unit 4 has a connector receiver 14 connected to a connection cable 13 on a front surface thereof. A connecting unit 17 with a cap is disposed in the base end of the connection cable 13. Further, the connector unit 16 is disposed in the extreme end of a universal cord 15 of the endoscope 2. An electrical connection portion of the connector unit 16 is detachably connected to the connecting unit 17 with the cap.

An image pick-up signal obtained in the image pick-up unit is sent to the image processing unit 4 through the connection cable 13 and converted to a video signal by the image processing unit 4. The video signal is displayed on the image display unit 5 as an image picked up by the endoscope 2.

Although the endoscope 2 is an electronic endoscope for picking up an endoscope image by an image pick-up portion (not shown image pick-up device) disposed in the extreme end of a later-described insertion portion 21, it may be, for example, a fiber endoscope using an image guide fiber. When the fiber endoscope is used, an optical image guided by the image guide fiber is picked up by a TV camera or the like.

Figure 2:
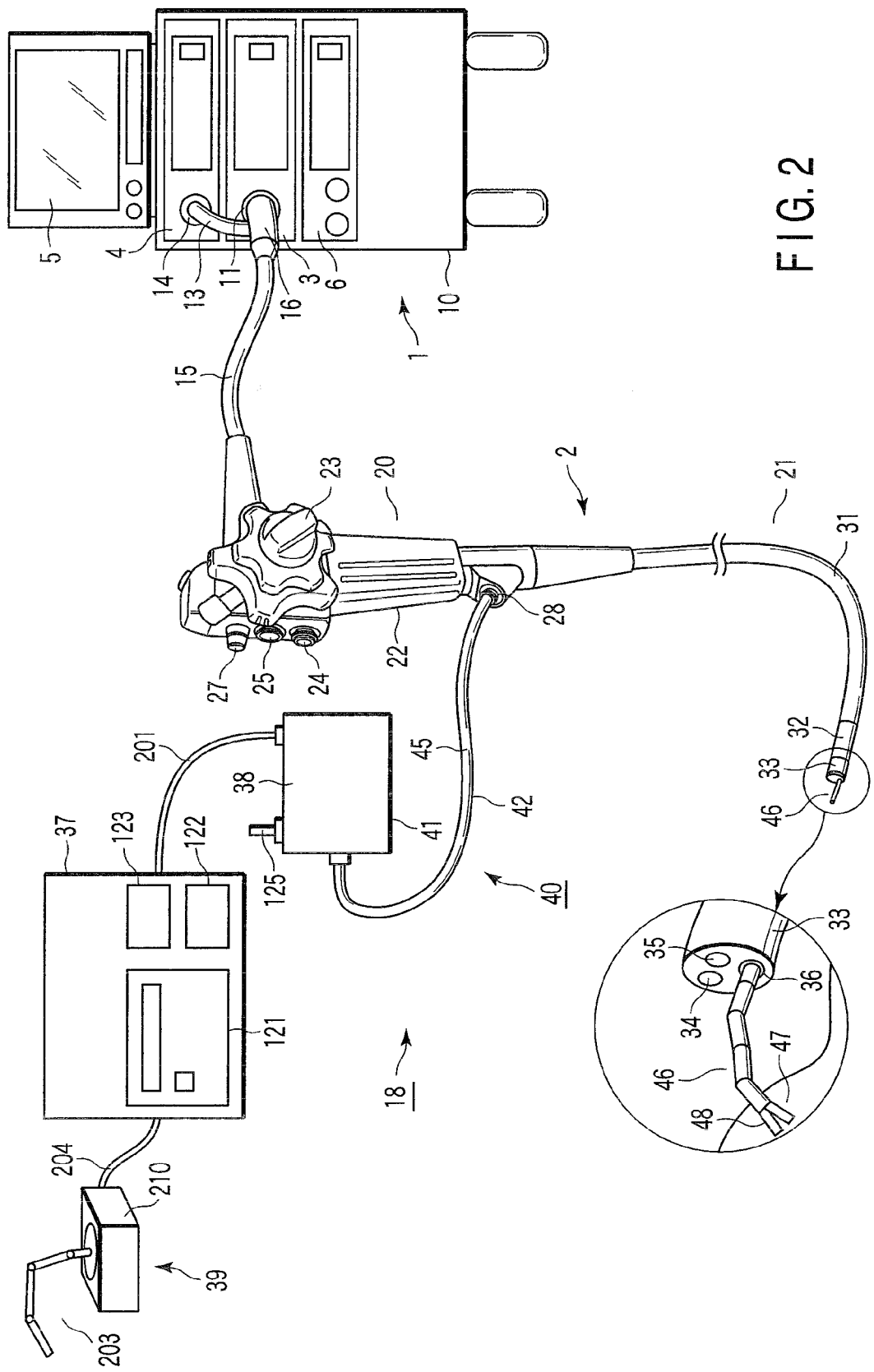
FIG. 2 is a perspective view schematically showing an endoscope and a surgical instrument in the endoscope system according to the embodiment.

As shown in FIGS. 1 and 2, the endoscope 2 has a manipulation portion 20 and the insertion portion 21 as a base member.

The universal cord 15 is connected to the manipulation portion 20. A grip portion 22 is disposed in the manipulation portion 20. The manipulation portion 20 is provided with various types of function manipulation members, such as an angle manipulation knob 23, an air/water feed manipulation button 24, a suction manipulation button 25, a gas supply manipulation button 26, and switches 27. The function manipulation members are disposed in portions nearer to a proximal end side than the position of the grip portion 22. Further, an insertion port 28 of an insertion channel, into which a later-described surgical instrument 40 and the like are inserted, is disposed in a portion which is positioned nearer to an extreme end side than the position of the grip portion 22.

As shown in FIGS. 1 and 2, the insertion portion 21 is composed of a flexible tube (soft portion) 31 positioned to the proximal end side, a bending portion 32 connecting to the extreme end of the flexible tube 31, and an extreme end portion 33 connected to the extreme end of the bending portion 32. The flexible tube 31 has elasticity and flexibility and is bent by an external force. The bending portion 32 is forcibly bend by manipulating the angle manipulation knob 23. The position and the direction of the extreme end portion 33 are changed by bending the bending portion 32 so that a desired observation target (affected area and the like) is captured in an observation field of view (or in an image pickup field of view).

As shown in FIG. 2, an observation window 34, an illumination window 35, and a channel port 36 are disposed in the extreme end surface portion of the extreme end portion 33.

An image pickup unit, which includes an optical system composed of an objective lens (not shown) and the like and an image pick-up device such as a CCD, is disposed inside the observation window 34. The image pick-up unit picks up an affected area and the like in a body cavity. An image pick-up signal obtained by the image pick-up unit is sent to the image processing unit 4 through the connection cable 13 as described above.

The channel port 36 communicates with the insertion port 28 through an insertion channel (not shown) formed in the insertion portion 21. The insertion channel is used as a path through which an insertion portion 42 of a multijointed surgical instrument 40 for an endoscope is inserted.

Although it is assumed in the embodiment that one surgical instrument 40 is inserted into one insertion channel, a plurality of surgical instruments 40 may be inserted into the one insertion channel. Further, it is also possible to provide a plurality of the insertion channels and to insert each of the surgical instruments 40 into each of the insertion channels.

Next, a surgical instrument extreme end movement controller 18 will be explained with reference to FIGS. 2, 3, 4, 5A and 5B. As shown in FIG. 2, the surgical instrument extreme end movement controller 18 includes a surgical instrument controller 37, a surgical instrument drive unit (motor unit) 38, a bending manipulation unit (manipulation input unit) 39, and the surgical instrument 40.

The surgical instrument 40 includes a manipulation unit 41 which can be gripped by an operator and the insertion portion 42 coupled with the manipulation unit 41.

The surgical instrument drive unit 38 is assembled to the manipulation unit 41.

As shown in FIG. 2, the insertion portion 42 is inserted into a body cavity through the insertion channel. The insertion portion 42 is composed of a flexible tube (soft portion) 45 which is positioned on the proximal end (base end) side, a bending portion 46 connected to the extreme end of the flexible tube 45, and an extreme end portion 47 connected to the extreme end of the bending portion 46.

The flexible tube 45 has elasticity and flexibility and is bent by an external force.

The bending portion 46 is bent by the manipulation unit 41.

The extreme end portion 47 is provided with a grip forceps 48 as a surgical instrument for operating on an affected area and the like.

Figure 4:
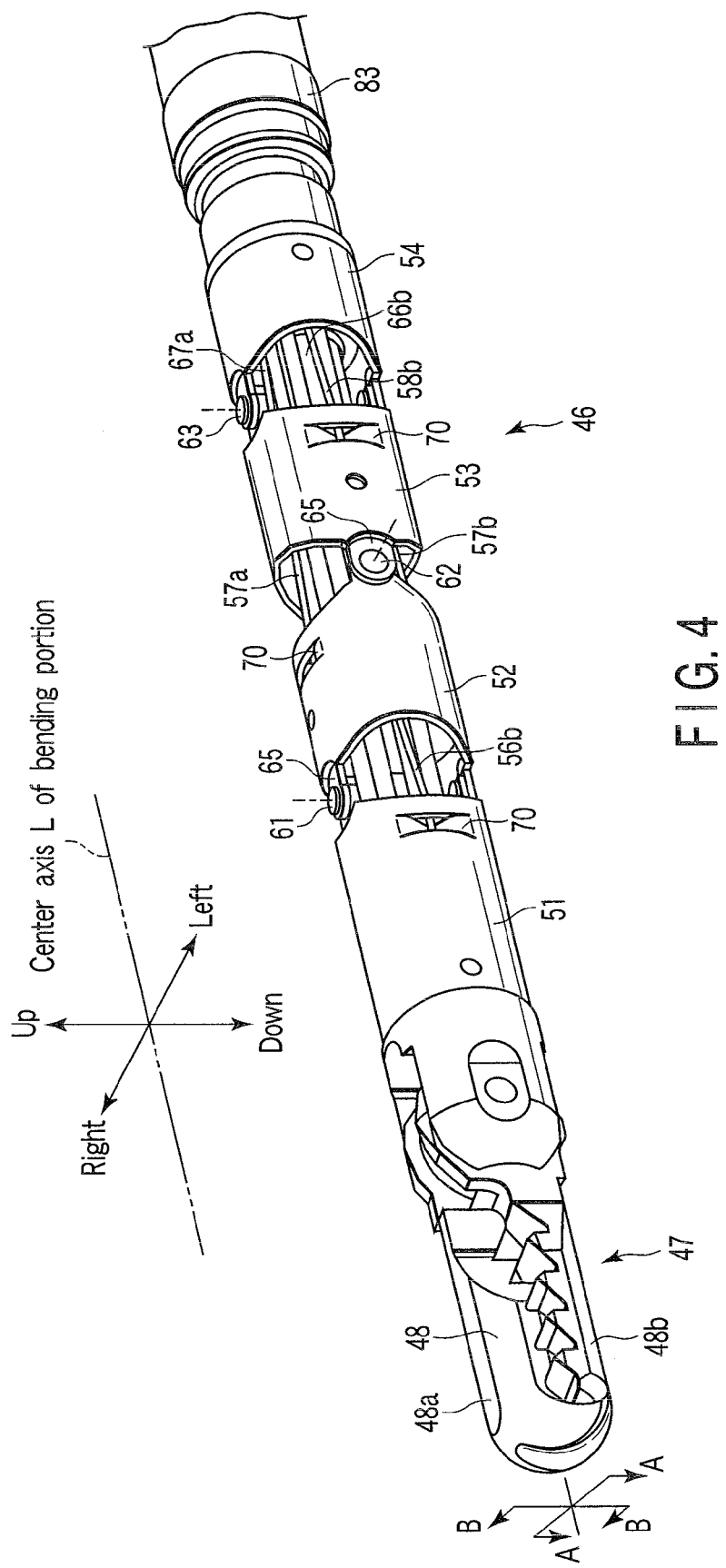
FIG. 4 is a perspective view showing an extreme end portion and a bending portion in an insertion portion of the surgical instrument according to the embodiment.

As shown in FIG. 4, the grip forceps 48 includes grip members 48a, 48b which are opened and closed up and down. The grip members 48a, 48b are opened and closed in up and down directions by a manipulation wire 93 inserted into the insertion portion 42. The extreme end portion 47 may be provided with a surgical instrument such as a high-frequency knife or a high-frequency solidifier in addition to the grip forceps 48.

As shown in FIGS. 4, 5A and 5B, the bending portion 46 includes the multijointed bending mechanism. The multi-jointed mechanism is constructed by coupling bending pieces 51, 52, 53, 54, 55. FIG. 4 is a perspective view showing the extreme end portion 47 and the bending portion 46. FIG. 5A is a horizontal longitudinal sectional view of the bending portion 46 along line A-A in FIG. 4 in the long axis direction of the insertion portion 42 as viewed from above. FIG. 5B is a vertical longitudinal sectional view of the bending portion 46 along line B-B in FIG. 4 in the long axis direction of the insertion portion 42 as viewed from the left side thereof. The up, down, right, and left directions of the bending portion 46 are as shown by indexes of FIG. 4.

The bending pieces 51, 52, 53, 54, 55 are formed of an annular member. As shown in FIG. 4, the bending pieces 51, 52, 53, 54, 55 are disposed by being coaxially arranged in a line in the long axis direction of the insertion portion 42. The bending pieces 51, 52, 53, 54, 55 are sequentially called a first bending piece 51, a second bending piece 52, a third bending piece 53, a fourth bending piece 54, and a fifth bending piece 55 from the extreme end side thereof.

As shown in FIG. 4, the first bending piece 51 is relatively rotatably coupled with the second bending piece 52 by the first rotation shaft 61 having a rotating shaft. As shown in FIG. 5B, a rotating shaft of the first rotation shaft 61 is disposed so that it is orthogonal to a center axis L of the bending portion 46 in a direction along up and down directions.

The first and second bending pieces 51, 52 are rotatably connected to each other around a first rotation shaft 61 and rotatably coupled with each other by the first rotation shaft 61. The axial direction of the first rotation shaft 61 is orthogonal to the long axis direction of the insertion portion 42 and the first rotation shaft 61 is disposed in a direction along the up and down directions shown in FIG. 4. Accordingly, the first and second bending pieces 51, 52 can be relatively rotated in right and left directions when viewed from the proximal end (base end) side in FIG. 4.

The second and third bending pieces 52, 53 are rotatably connected to each other around a second rotation shaft 62 and rotatably coupled with each other by the second rotation shaft 62. The axial direction of the second rotation shaft 62 is orthogonal to the long axis direction of the insertion portion 42 and the second rotation shaft 62 is disposed in a direction along the right and left directions shown in FIG. 4. Accordingly, the second and third bending pieces 52, 53 can be relatively rotated in the up and down directions when viewed from the proximal end (base end) side in FIG. 4.

The third and fourth bending pieces 53, 54 are rotatably connected to each other around a third rotation shaft 63 and rotatably coupled with each other by the third rotation shaft 63. The axial direction of the third rotation shaft 63 is orthogonal to the long axis direction of the insertion portion 42 and the third rotation shaft 63 is disposed in the direction along the up and down directions shown in FIG. 4. Accordingly, the third and fourth bending pieces 53, 54 can be relatively rotated in the right and left directions when viewed from the proximal end (base end) side in FIG. 4.

The fourth bending piece 54 is rotatably coupled with the fifth bending piece 55 by a fourth rotation shaft 64. The axial direction of the fourth rotation shaft 64 is orthogonal to the long axis direction of the insertion portion 42 and the fourth rotation shaft 64 is disposed in a direction along the right and left directions shown in FIG. 4. Accordingly, the fourth bending piece 54 and the fifth bending piece 55 can be relatively rotated in the up and down directions when viewed from a proximal end (base end) side in FIG. 4.

That is, the first rotation shaft 61 constitutes a joint for relatively rotating the first and second bending pieces 51, 52 in the right and left directions. The second rotation shaft 62 constitutes a joint for relatively rotating the second and third bending pieces 52, 53 in the up and down directions. The third rotation shaft 63 constitutes a joint for relatively rotating the third and fourth bending pieces 53, 54 in the right and left directions. Further, the fourth rotation shaft 64 constitutes a joint for relatively rotating the fourth and fifth bending pieces 54, 55 in the up and down directions.

In the embodiment, the axial directions of the first, second, third, and fourth rotation shafts 61, 62, 63, 64 are alternately offset by 90°. That is, the bending pieces 51, 52 and the bending pieces 53, 54 are rotated in the right and left directions. The bending pieces 52, 53 and the bending pieces 54, 55 are rotated in the up and down directions. Further, the axial directions of the rotation shafts 61, 62, 63, 64 are orthogonal to the center axis (long axis) L of the bending portion 46 (refer to FIGS. 4, 5A and 5B). The center axis L agrees with the long axis of the insertion portion 42.

As shown in FIGS. 5A and 5B, the bending pieces 51, 52, 53, 54, 55 have tongue-piece-shaped coupling portions 65 projecting from the end edges thereof. When the coupling portions 65 are overlapped with each other, the rotation shafts 61, 62, 63, 64 pass through the overlapping portions. That is, the rotation shafts 61, 62, 63, 64 are rivet-like shaft members.

The multijointed bending mechanism arranged as described above is covered with a flexible casing (not shown). The bending portion 46 is constructed by this configuration.

A first set of a pair of non-expandable manipulation wires 56 (56a, 56b) connected to the first bending piece 51, a second set of a pair of non-expandable manipulation wires 57 (57a, 57b) connected to the second bending piece 52, a third set of a pair of non-expandable manipulation wires 58 (58a, 58b) connected to the third bending piece 53, and a fourth set of a pair of non-expandable manipulation wires 59 (59a, 59b) connected to the fourth bending piece 54 are inserted into the insertion portion 42.

As shown in FIG. 5A, the manipulation wires 56a, 56b are laterally symmetrically disposed in the bending portion 46 with respect to the center axis L. The extreme ends of the manipulation wires 56a, 56b extend to the region in the first bending piece 51 and are connected to the first bending piece 51.

The direction of the center axis of the first bending piece 51 approximately agrees with the direction of the center axis L. On one plane which passes through both the direction of the center axis of the first bending piece 51 and the axial direction of the first rotation shaft 61, the right half portion of the first bending piece 51 is called a right portion, and the left half portion of the first bending piece 51 is called a left portion.

The extreme end of the manipulation wire 56a described above is connected to the right portion of the first bending piece 51. Further, the extreme end of the manipulation wire 56b is connected to the left portion of the first bending piece 51. When the manipulation wire 56a is pulled to the base end (proximal end) side shown in FIG. 5A, the first bending piece 51 is rotated rightward around the first rotation shaft 61. Further, when the manipulation wire 56b is pulled to the base end side, the first bending piece 51 is rotated leftward around the first rotation shaft 61. As described above, the manipulation wires 56 rotate the first bending piece 51.

As shown in FIG. 5B, the manipulation wires 57a, 57b are vertically symmetrically disposed in the bending portion 46 with respect to the center axis L. The extreme ends of the manipulation wires 57a, 57b extend to the region in the second bending piece 52 and are connected to the second bending piece 52.

The direction of the center axis of the second bending piece 52 approximately agrees with the direction of the center axis L. On one plane which passes through both the direction of the center axis of the second bending piece 52 and the axial direction of the second rotation shaft 62, the upper half portion of the second bending piece 52 is called an upper portion, and the lower half portion of the second bending piece 52 is called a lower portion.

The extreme end of the manipulation wire 57a described above is connected to the upper portion of the second bending piece 52. Further, the extreme end of the manipulation wire 57b is connected to the lower portion of the second bending piece 52. When the manipulation wire 57a is pulled to the base end (proximal end) side shown in FIG. 5B, the second bending piece 52 is rotated upward around the second rotation shaft 62. Further, when the manipulation wire 57b is pulled to the base end side shown in FIG. 5B, the second bending piece 52 is rotated downward around the second rotation shaft 62. As described above, the manipulation wires 57 rotate the second bending piece 52.

As shown in FIG. 5A, the manipulation wires 58a, 58b are laterally symmetrically disposed in the bending portion 46 with respect to the center axis L. The extreme ends of the manipulation wires 58a, 58b extend to the region in the third bending piece 53 and are connected to the third bending piece 53.

The direction of the center axis of the third bending piece 53 approximately agrees with the direction of the center axis L. On one plane which passes through both the direction of the center axis of the third bending piece 53 and the axial direction of the third rotation shaft 63, the right half portion of the third bending piece 53 is called a right portion, and the left half portion of the third bending piece 53 is called a left portion.

The extreme end of the manipulation wire 58a described above is connected to the right portion of the third bending piece 53. Further, the extreme end of the manipulation wire 58b is connected to the left portion of the third bending piece 53. When the manipulation wire 58a is pulled to the base end (proximal end) side shown in FIG. 5A, the third bending piece 53 is rotated rightward around the third rotation shaft 63. Further, when the manipulation wire 58b is pulled to the base end side shown in FIG. 5A, the third bending piece 53 is rotated leftward around the third rotation shaft 63. As described above, the manipulation wire 58 rotates the third bending piece 53.

As shown in FIG. 5B, the manipulation wires 59a, 59b are vertically symmetrically disposed in the bending portion 46 with respect to the center axis L. The extreme ends of the manipulation wires 59a, 59b extend to the region in the fourth bending piece 54 and are connected to the fourth bending piece 54.

The direction of the center axis of the fourth bending piece 54 approximately agrees with the direction of the center axis L. On one plane which passes through both the direction of the center axis of the fourth bending piece 54 and the axial direction of the fourth rotation shaft 64, the upper half portion of the fourth bending piece 54 is called an upper portion, and the lower half portion of the fourth bending piece 54 is called a lower portion.

The extreme end of the manipulation wire 59a described above is connected to the upper portion of the fourth bending piece 54. Further, the extreme end of the manipulation wire 59b is connected to the lower portion of the fourth bending piece 54. When the manipulation wire 59a is pulled to the base end (proximal end) side shown in FIG. 5B, the fourth bending piece 54 is rotated upward around the fourth rotation shaft 64. Further, when the manipulation wire 59b is pulled to the base end side shown in FIG. 5B, the fourth bending piece 54 is rotated downward around the fourth rotation shaft 64. As described above, the manipulation wires 59 rotate the fourth bending piece 54.

As described above, the pairs of the manipulation wires 56, 57, 58, 59, which individually correspond to each other, are connected to the bending pieces 51, 52, 53, 54. When the pairs of the manipulation wires 56, 57, 58, 59 are appropriately selected and pushed and pulled in the bending portion 46, the bending pieces 51, 52, 53, 54 are independently rotated.

Various methods can be employed to connect the extreme ends of the manipulation wires 56, 57, 58, 59 to the bending pieces 51, 52, 53, 54. The connection is made as described below in the embodiment.

As shown in FIG. 5A, in the base end portion of the first bending piece 51, cut and raised pieces 70, which project inside of the first bending piece 51, are formed in the right portion and the left portion of the first bending piece 51. The extreme end of the manipulation wire 56a is inserted into the cut and raised piece 70 in the right portion, and fixed to the cut and raised piece 70 by brazing. Further, the extreme end of the manipulation wire 56b is inserted into the cut and raised piece 70 in the left portion, and fixed to the cut and raised piece 70 by brazing.

As shown in FIG. 5B, in the base end portion of the second bending piece 52, cut and raised pieces 70, which project inside of the second bending piece 52, are formed in the upper portion and the lower portion of the second bending piece 52. The extreme end of the manipulation wire 57a is inserted into the cut and raised piece 70 in the upper portion, and fixed to the cut and raised piece 70 by brazing. Further, the extreme end of the manipulation wire 57b is inserted into the cut and raised piece 70 in the lower portion, and fixed to the cut and raised piece 70 by brazing.

As shown in FIG. 5A, cut and raised pieces 80, which are recessed to the inside of the third bending piece 53, are formed in the right side portion and the left side portion of the third bending piece 53 around the peripheral edge of the base end side of the third bending piece 53. The extreme end of the manipulation wire 58a is inserted into the cut and raised piece 80 of the right side portion and fixed to the cut and raised piece 80 by brazing. Further, the extreme end of the manipulation wire 58b is inserted into the cut and raised piece 80 of the left side portion and fixed to the cut and raised piece 80 by brazing.

Further, as shown in FIG. 5B, cut and raised pieces 91, which are recessed to the inside of the fourth bending piece 54, are formed in the upper side portion and the lower side portion of the fourth bending piece 54 around the peripheral edge of the base end side of the fourth bending piece 54. The extreme end of the manipulation wire 59a is inserted into the cut and raised piece 91 of the upper side portion and fixed thereto by brazing. Further, the extreme end of the manipulation wire 59*b* is inserted into the cut and raised piece 91 of the lower side portion and fixed thereto by brazing.

The manipulation wires 56 are inserted into a guide sheath 66, the manipulation wires 57 are inserted into a guide sheath 67, the manipulation wires 58 are inserted into a guide sheath 68, and the manipulation wires 59 are inserted into a guide sheath 69, and they are individually guided up to the manipulation unit 41. The guide sheaths 66, 67, 68, 69 have flexibility and are formed of a sheath-like elastic member having elasticity; for example, an intimately wound coil, a resin tube, and the like. Inner holes of the guide sheaths 66, 67, 68, 69 act as guide members for guiding the direction of travel of the manipulation wires 56, 57, 58, 59.

The extreme end of each guide sheath is not connected to a bending piece to which the manipulation wire to be guided by the guide sheath itself is connected but connected to a bending piece disposed nearer to the base end side than the above bending piece. For example, the extreme ends of guide sheaths 66*a*, 66*b* are connected to the second bending piece 52. The extreme ends of guide sheaths 67*a*, 67*b* are connected to the third bending piece 53. Further, the extreme ends of guide sheaths 68*a*, 68*b* are connected to the fourth bending piece 54.

Figure 7A:
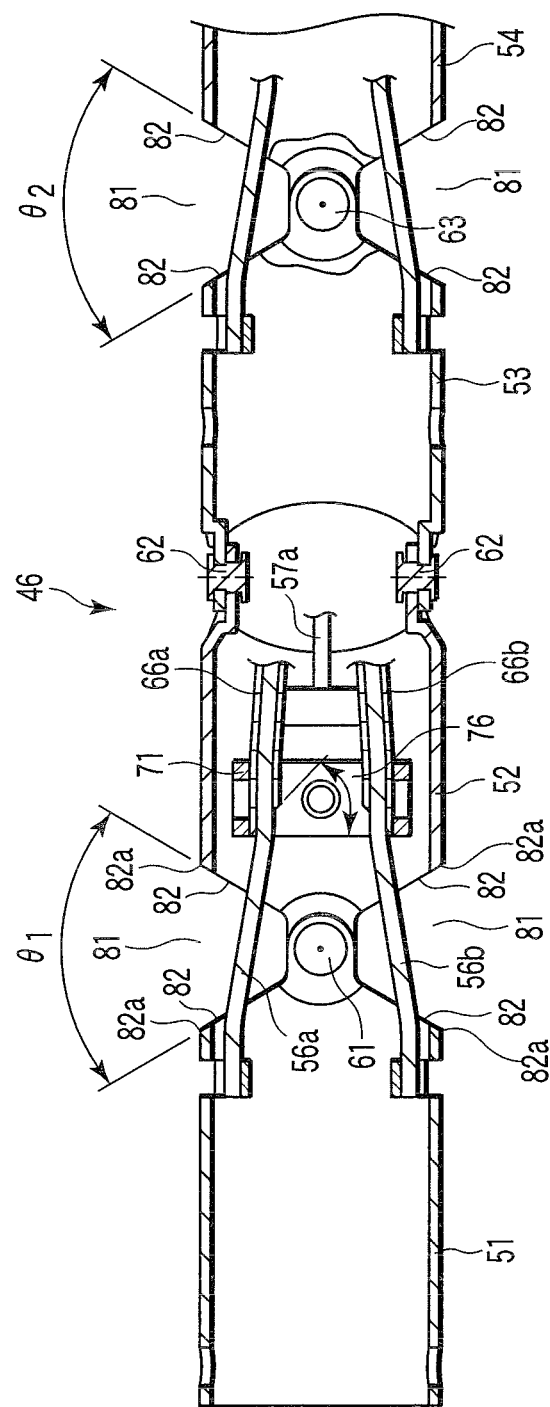
FIG. 7A shows the angular relationship under which bending pieces rotate and is a longitudinal sectional view of the bending portion from above.
Figure 7B:
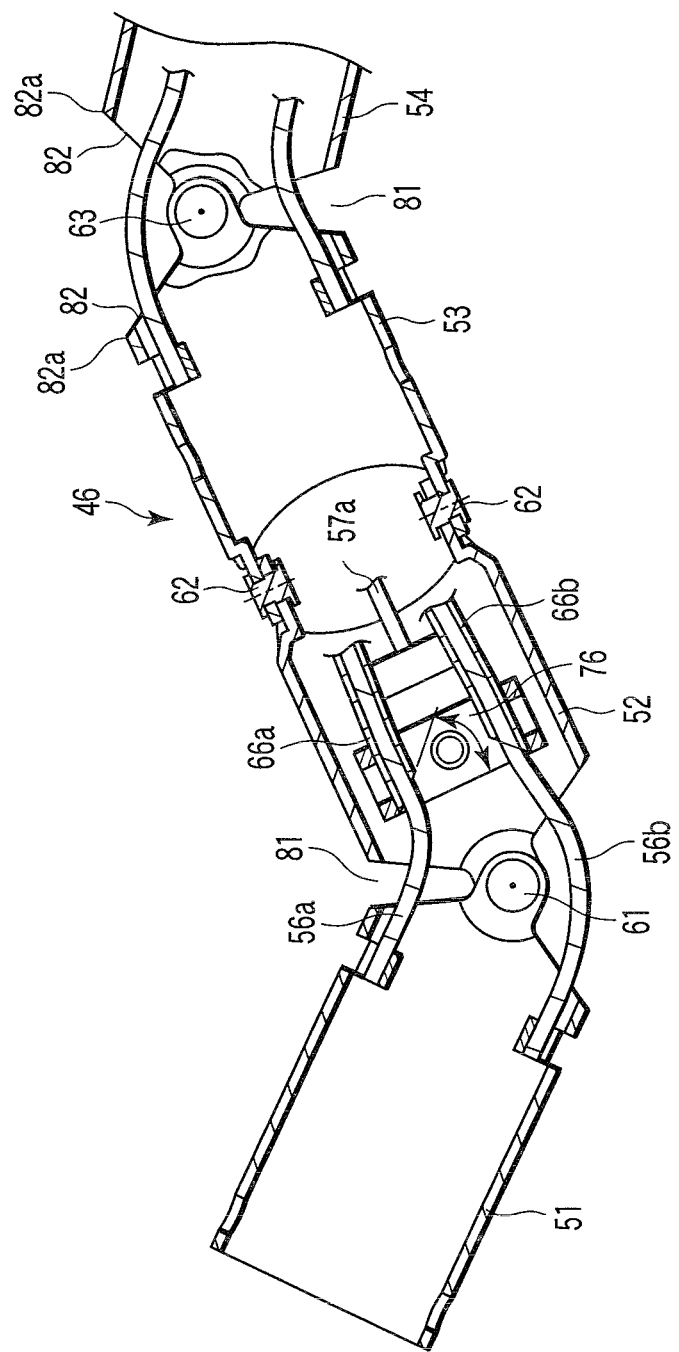
FIG. 7B shows the angular relationship under which the bending pieces rotate and is a longitudinal sectional view of the bending portion as viewed from above.

Note that base ends of the guide sheaths may be connected to the base end portion of the bending portion 46 (the extreme end of the flexible tube 45). Further, as shown in FIGS. 7A and 7B, the most extreme end faces of the guide sheaths 66*a*, 66*b* may have slant surfaces whose sides near the center of the bending portion 46 retreat to the base end side than the side thereof near the outer periphery of the bending portion 46. As described above, the guide sheaths 66*a*, 66*b* may be arranged so that they avoid interference with contained members.

Next, the angular relationship under which the respective bending pieces mutually rotate will be explained with reference to FIGS. 7A and 7B.

The end faces 82, which confront each other (which are adjacent to each other) in adjacent bending pieces, form a gap 81. The gap 81 expands in a fan-shape at an angle θ around the axis of a rotation shaft. In more detail, lines extending from the end faces 82 intersect on the axis of the rotation shaft. Accordingly, the respective end faces 82 are formed as linear end edges passing through the rotation axis, respectively. Then, the gap 81 is formed by the two end faces 82 confronting each other and expanding in a fan-shape at an angle θ about an intersecting point (axis of the rotation shaft).

Note that the extended lines need not necessarily intersect on the axis of the rotation shaft, and the respective end faces 82 may not be formed as linear end edges passing through the rotation axis, respectively. In this case, the gap 81, which expands in a fan-shape at the angle θ, may be preferably formed by the lines which pass through ends (apexes) 82*a*, which are positioned at the most external sides of the end faces 82, and the axis of the rotation shaft.

Note that the sum of the angles θ of the gaps 81 of at least two adjacent bending pieces in the bending pieces rotating in the same direction is set to 90° or more. As shown in, for example, FIGS. 7A and 7B, the sum of the rotatable angle θ1 of the gap 81 between the bending pieces 51, 52 rotating in the same direction and the rotatable angle θ2 of the gap 81 between the bending pieces 53, 54 rotating in the same direction is set to 90° or more.

As described above, the rotatable angle θ of the multijointed bending piece may be preferably allocated not only to one gap 81 but also to the gaps 81 between the bending pieces rotating in the same direction (a plurality of adjacent gaps 81). With this configuration, it is not necessary to increase the angle θ in one gap 81. Accordingly, the maximum angle θ formed by one gap 81 is reduced. As a result, the amount of rotation of a bending piece in one gap 81 is reduced. Thus, when a bending operation causes the contained members such as the manipulation wires and the guide sheaths to traverse the gap 81, they are less likely to be caught by the gap 81.

Next, how the manipulation wires and the guide sheaths are disposed in the bending pieces will be explained with reference to FIGS. 5A, 5B, 6A, 6B, 6C, and 6D.

Figure 6A:
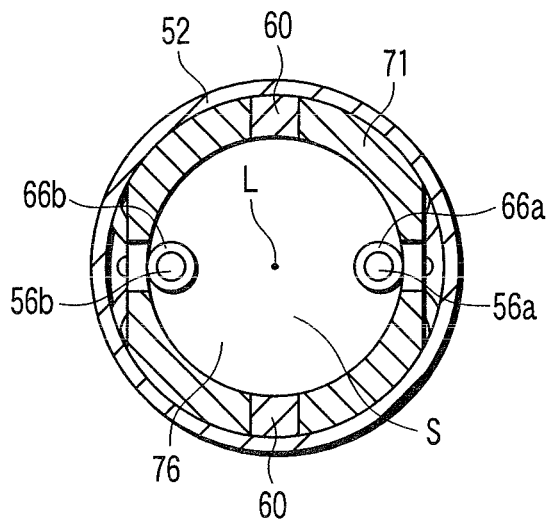
FIG. 6A is a lateral sectional view along a line A-A in FIG. 5B and a view showing the disposition of manipulation wires and guide sheaths.

The extreme ends of the guide sheaths 66*a*, 66*b* are fixed to a first wire guide 71 disposed in the second bending piece 52 and positioned to and supported by the second bending piece 52. The first wire guide 71 is formed of, for example, a ring-like sheet-shaped member as shown in FIGS. 5A, 5B and 6A. The first wire guide 71 is fixed to the inner wall of the second bending piece 52 by pins 60 at both the upper and lower end edges thereof. Cut-outs are formed in both the right and left ends of the first wire guide 71 as shown in FIG. 6A. An insertion hole 76, through which contained members such as the guide sheaths 66*a*, 66*b* are inserted, is formed at the center of the first wire guide 71. The insertion hole 76 is formed in an approximately circular shape about the center axis L. The extreme ends of the guide sheaths 66*a*, 66*b* are positioned and disposed in, for example, the right/left inner wall portions in the insertion hole 76, respectively and fixed to the portions by brazing or the like. Accordingly, the extreme ends of the guide sheaths 66*a*, 66*b* are disposed in the same distance from the center axis L. In other words, the extreme ends of the guide sheaths 66*a*, 66*b* are bilaterally symmetrically disposed across the center axis L. With this configuration, the manipulation wires 56*a*, 56*b* inserted into the guide sheaths 66*a*, 66*b* are also bilaterally symmetrically disposed across the center axis L. That is, the first wire guide 71 plays a role as positioning/disposing mechanism for positioning and disposing the manipulation wires 56*a*, 56*b* and the guide sheaths 66*a*, 66*b*.

After the manipulation wires 56*a*, 56*b* project from the extreme ends of the guide sheaths 66*a*, 66*b* as shown in FIG. 5A, they enter the first bending piece 51 while extending, for example, right and left. The manipulation wire 56*a* is inserted into the cut and raised piece 70 in the right portion as described above. The manipulation wire 56*b* is inserted into the cut and raised piece 70 in the left portion as described above.

Note that although the extreme ends of the guide sheaths 66*a*, 66*b* are directly fixed to the first wire guide 71, they may be indirectly fixed to the first wire guide 71 using a connector such as a connecting ring, not shown.

Figure 6B:
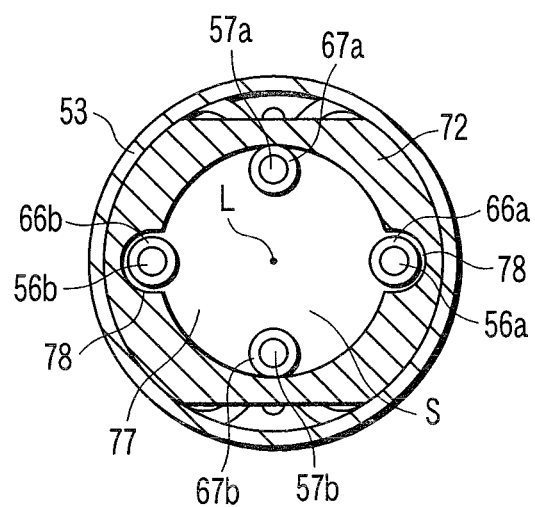
FIG. 6B is a lateral sectional view along a line B-B in FIG. 5B and a view showing the disposition of the manipulation wires and the guide sheaths.

As shown in FIGS. 5A, 5B and 6B, the extreme ends of the guide sheaths 67*a*, 67*b* are fixed to a second wire guide 72 disposed in the third bending piece 53 and positioned to and supported by the third bending piece 53. The second wire guide 72 is formed of, for example, a ring-like sheet-shaped member. The second wire guide 72 is fixed to the inner wall of the third bending piece 53 by pins 60 at both the end edges thereof. As shown in FIG. 6B, cut-outs are formed in the upper and lower end edges of the outer peripheral portion of the second wire guide 72. Guide sheaths 67*a*, 67*b* are brazed to the cut-outs. That is, the cut-outs are brazed portions.

An insertion hole 77, through which the contained members such as the guide sheaths 66*a*, 66*b* and the guide sheaths 67*a*, 67*b* are inserted, is formed at the center of the second wire guide 72. The insertion hole 77 is formed in a circular shape about the center axis L. The radius of the insertion hole 77 is smaller than that of the insertion hole 76. The extreme ends of the guide sheaths 67*a*, 67*b* are positioned and disposed in, for example, the upper/lower inner wall portions in the insertion hole 77, respectively and fixed to the positions by brazing or the like. Accordingly, the extreme ends of the guide sheaths 67a, 67b are disposed at the same distance from the center axis L. In other words, the extreme ends of the guide sheaths 67a, 67b are vertically symmetrically disposed with respect to the center axis L. With this configuration, the manipulation wires 57a, 57b passing through the guide sheaths 67a, 67b are also vertically symmetrically disposed with respect to the center axis L. As described above, the second wire guide 72 plays a role as positioning/disposing mechanism for positioning and disposing the manipulation wires 57a, 57b and the guide sheaths 67a, 67b.

Further, as shown in FIG. 6B, groove portions 78 are formed in the right/left inner wall portions in the insertion hole 77. The guide sheath 66a is fitted into the groove portion 78 in the right inner wall portion so that it is free to advance and retreat. Further, the guide sheath 66b is fitted into the groove portion 78 in the left inner wall portion so that it is free to advance and retreat. With this configuration, the guide sheaths 66a, 66b are positioned and held by the second wire guide 72. At this time, the guide sheaths 67a, 67b are disposed inwards of the guide sheaths 66a, 66b (nearer to the center axis L) with respect to a direction vertical to the axial direction of the first rotation shaft 61 and the second rotation shaft 62 (in the direction of the center axis L). Accordingly, the manipulation wires 57a, 57b are disposed inwards of the manipulation wires 56a, 56b with respect to the direction of the center axis L. That is, in this case, the second wire guide 72 plays a role as positioning/disposing mechanism for executing positioning so that the guide sheaths 67a, 67b are disposed inwards of the guide sheaths 66a, 66b (the manipulation wires 57a, 57b are disposed inwards of the manipulation wires 56a, 56b).

After the manipulation wires 57a, 57b, which are guided by the guide sheaths 67a, 67b, project from the extreme ends of the guide sheaths 67a, 67b as shown in FIG. 5B, they enter the second bending piece 52 while extending, for example, up and down. The manipulation wire 57a is inserted into the cut and raised piece 70 in the upper portion as described above. The manipulation wire 57b is inserted into the cut and raised piece 70 in the lower portion as described above.

Note that although the extreme ends of the guide sheaths 67a, 67b are directly fixed to the second wire guide 72, they may be indirectly fixed to the second wire guide 72 using a connector such as a connecting ring, not shown.

In the third bending piece 53, the guide sheaths 67a, 67b are disposed inwards of the guide sheaths 66a, 66b (nearer to the center axis L) as shown in FIG. 6B. Accordingly, a space S is formed around the periphery of the center axis L. Contained members, a surgical function unit to be assembled to the extreme end portion 47 (for example, the grip forceps 48), and the like are disposed in the space S.

As shown in FIGS. 4, 5A and 5B, cut and raised pieces 79, which are recessed to the inside of the fourth bending piece 54, are formed in the right inner wall portion and the left inner wall portion in the end edge portion of the extreme end of the fourth bending piece 54. The extreme end of the guide sheath 68a is fixed to the cut and raised piece 79 in the right inner wall portion by brazing or the like. The extreme end of the guide sheath 68b is fixed to the cut and raised piece 79 in the left inner wall portion by brazing or the like.

Note that the extreme ends of the guide sheaths 68a, 68b may be fixed to the fourth bending piece 54 by connection rings (not shown).

As shown in FIG. 5A, after the manipulation wires 58a, 58b project from the extreme ends of the guide sheaths 68a, 68b, they enter the third bending piece 53. As described above, the manipulation wire 58a is inserted into the cut and raised piece 80 in the right side portion. Further, the manipulation wire 58b is inserted into the cut and raised piece 80 in the left side portion as described above.

Note that the extreme ends of the manipulation wires 58a, 58b may be fixed to the third bending piece 53 by connection rings (not shown).

Figure 6C:
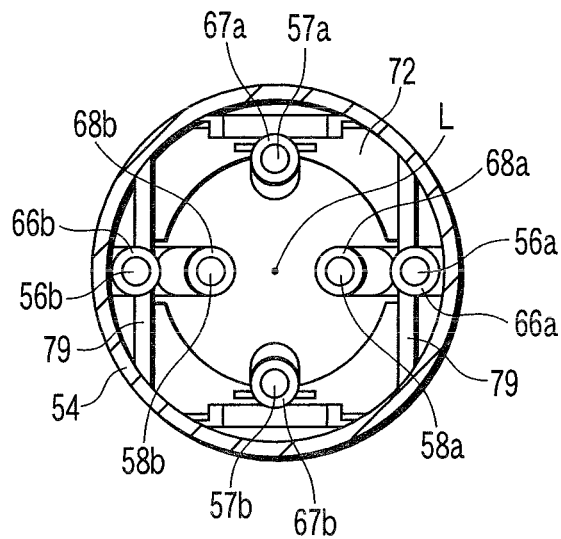
FIG. 6C is a lateral sectional view along a line C-C in FIG. 5B and a view showing the disposition of the manipulation wires and the guide sheaths.

As shown in FIGS. 4, 5A and 6C, in the cut and raised pieces 80 and 79, the guide sheaths 66a, 66b are disposed more away externally from the center axis L than the cut and raised pieces 80, 79. To explain in detail, as shown in FIGS. 4 and 5A, the cut and raised pieces 80 have cut-out gaps 80a formed thereon, through which the guide sheaths 66a, 66b can be inserted. Further, the cut and raised pieces 79 have cut-out gaps 79a formed thereon, through which the guide sheaths 66a, 66b can be inserted. As shown in FIG. 4, the guide sheaths 66a, 66b pass through the cut-out gaps 80a from the inside of the third bending piece 53 and exit to the outside of the third bending piece 53. Further, the guide sheaths 66a, 66b reach the cut and raised pieces 79, pass through the cut-out gaps 79a, and enter the fourth bending piece 54.

Accordingly, as shown in FIG. 6C, the guide sheaths 68a, 68b are disposed inwards of the guide sheaths 66a, 66b (nearer to the center axis L) in a direction vertical to the axial direction of the first rotation shaft 61, the second rotation shaft 62, and the third rotation shaft 63 (in the direction of the center axis L). Therefore, the manipulation wires 58a, 58b are disposed inwards of the manipulation wires 56a, 56b in the direction of the center axis L. Thus, the cut and raised pieces 79, 80 play a role as positioning/disposing mechanism for executing positioning of the manipulation wires 58a, 58b and the guide sheaths 68a, 68b.

Further, as shown in FIG. 6C, the guide sheaths 68a, 68b are disposed inwards of the guide sheaths 66a, 66b and the guide sheaths 67a, 67b (nearer to the center axis L) in a direction vertical to the axial direction of the first rotation shaft 61, the second rotation shaft 62, and the third rotation shaft 63 (in the direction of the center axis L). Accordingly, the manipulation wires 58a, 58b are disposed inwards of the manipulation wires 56a, 56b and the manipulation wires 57a, 57b.

As shown in FIGS. 4 and 5B, cut and raised pieces 90, which are recessed to the inside of the fifth bending piece 55, are formed in the upper inner wall portion and the lower inner wall portion of the fifth bending piece 55 in the end edge portion of the fifth bending piece 55 on the extreme end side thereof. The extreme end of the guide sheath 69a is fixed to the cut and raised piece 90 in the upper inner wall portion by brazing or the like. The extreme end of the guide sheath 69b is fixed to the cut and raised piece 90 in the lower inner wall portion by brazing or the like.

Note that the extreme ends of the guide sheaths 69a, 69b may be fixed to the fifth bending piece 55 by connection rings (not shown).

As shown in FIG. 5B, after the manipulation wires 59a, 59b project from the extreme ends of the guide sheaths 69a, 69b, they enter the fourth bending piece 54. As described above, the manipulation wire 59a is inserted into the cut and raised piece 91 in the upper side portion. Further, the manipulation wire 59b is inserted into the cut and raised piece 91 in the lower side portion as described above.

As shown in FIG. 4, in the cut and raised pieces 91 and the cut and raised pieces 90, the guide sheaths 67a, 67b are disposed more away externally from the center axis L than the cut and raised pieces 91, 90. To explain in detail, as shown in FIG. 4, the cut and raised pieces 91 have cut-out gaps 91a formed thereon, through which the guide sheaths 67*a*, 67*b* can be inserted. Further, the cut and raised pieces 90 have cut-out gaps 90*a* formed thereon, through which the guide sheaths 67*a*, 67*b* can be inserted. As shown in FIG. 4, the guide sheaths 67*a*, 67*b* pass through the cut-out gaps 91*a* from the inside of the fourth bending piece 54 and exit to the outside of the fourth bending piece 54. Further, the guide sheaths 67*a*, 67*b* reach the cut and raised pieces 90, pass through the cut-out gaps 90*a*, and enter the fifth bending piece 55.

Figure 6D:
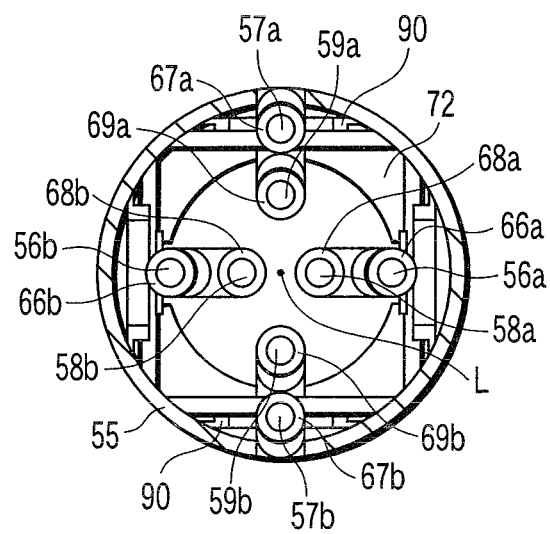
FIG. 6D is a lateral sectional view along a line D-D in FIG. 5B and a view showing the disposition of the manipulation wires and the guide sheaths.

Accordingly, as shown in FIG. 6D, the guide sheaths 69*a*, 69*b* are disposed inwards of the guide sheaths 67*a*, 67*b* in a direction vertical to the axial direction of the first rotation shaft 61, the second rotation shaft 62, the third rotation shaft 63 and the fourth rotation shaft 64 (in the direction of the center axis L). Accordingly, the manipulation wires 59*a*, 59*b* are disposed inwards of the manipulation wires 57*a*, 57*b* in the direction of the center axis L. Thus, the cut and raised pieces 91, 90 play a role as positioning/disposing mechanism for executing positioning of the manipulation wires 59*a*, 59*b* and the guide sheaths 69*a*, 69*b*.

As described above, the wire guides and the cut and raised pieces play the role as the positioning/disposing mechanism for specifying the positions of the guide sheaths and at the same time play the role as the positioning/disposing mechanism for determining the positions of the manipulation wires which are individually guided by the guide sheaths.

As shown in FIG. 4, the fifth bending piece 55 is a bending piece positioned at the most extreme base end of the bending portion 46. That is, it is possible to assume that the fifth bending piece 55 is the base end portion of the bending portion 46. A connector member 94 such as a connection ring is disposed in the extreme end of the flexible tube 45. The fifth bending piece 55 is coupled with the connector member 94. Further, the fifth bending piece 55 may be rotatably coupled with the connector member 94. In this mode, it is also possible to assume that the connector member 94 is the base end portion of the bending portion 46.

Further, the contained members such as a manipulation wire 93 and an electric wire are disposed in the space of the bending pieces in which the manipulation wires, the guide sheaths, and the positioning/disposing mechanism are not disposed. Further, the guide sheath and the manipulation wire on the base end side are disposed inwards of the guide sheath and the manipulation wire on the extreme end side. Accordingly, the space S is formed in a central region (in the periphery of the center axis L) of the bending piece on the extreme end side. In particular, the large space S is formed from the first bending piece 51 to the third bending piece 53. Thus, the contained members, the surgical function unit to be assembled to the extreme end portion 47 (for example, the grip forceps 48), and the like are disposed in the space S. Further, function parts such as an actuator and a sensor may be disposed in the space S.

Figure 3:
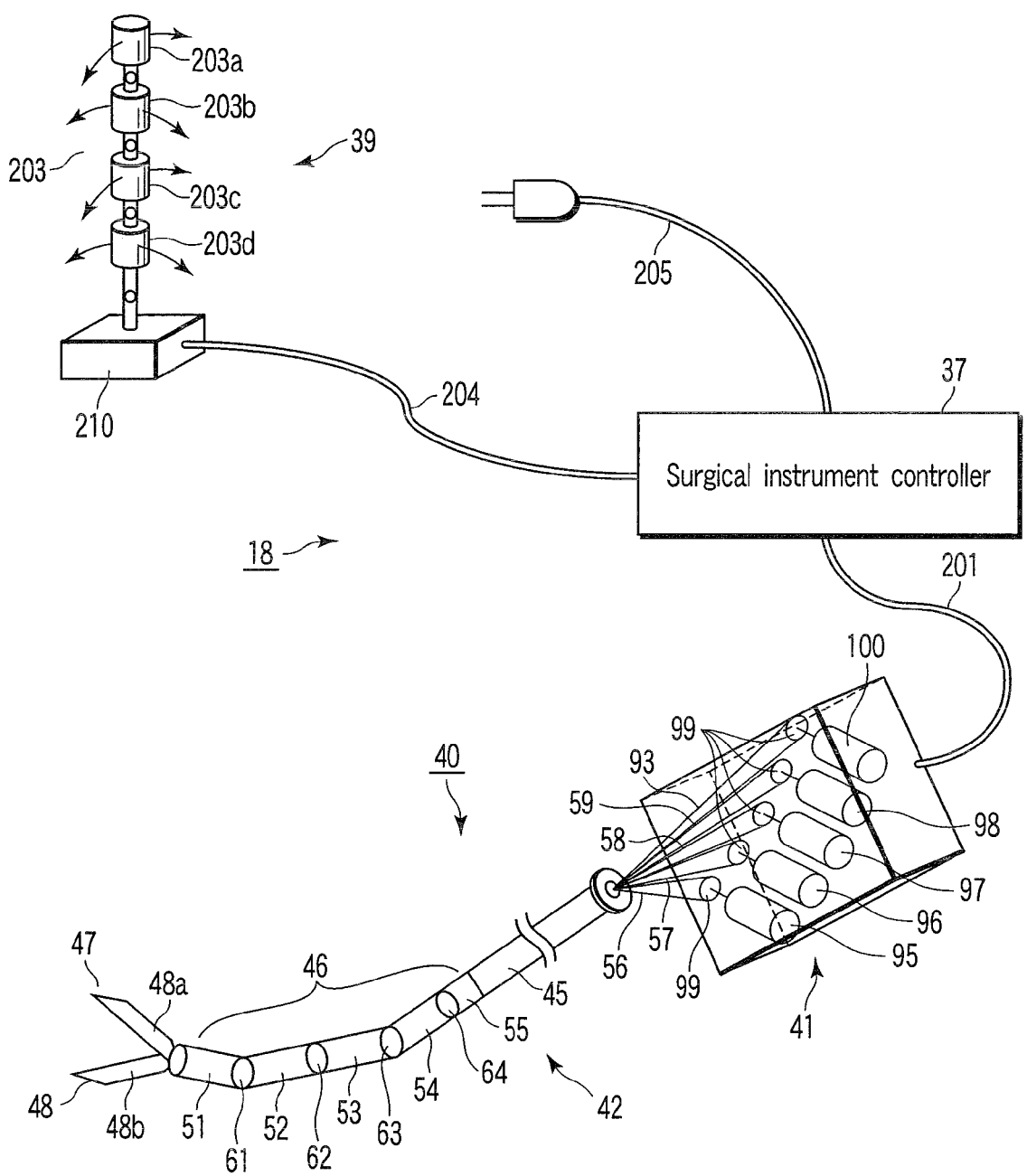
FIG. 3 is a perspective view schematically showing the surgical instrument according to the embodiment.

As shown in FIG. 3, the manipulation unit 41 is provided with a bending portion manipulation mechanism and a surgical portion manipulation mechanism. The bending portion manipulation mechanism is provided with drive motors 95, 96, 97, 98 for pushing and pulling the manipulation wires 56, 57, 58, 59, respectively. Further, the surgical portion manipulation mechanism is provided with a drive motor 100 for pushing and pulling the manipulation wire 93. The manipulation wires 56, 57, 58, 59 correspond to the bending pieces (targets to be rotated) 51, 52, 53, 54 and execute rotating manipulations. The manipulation wire 93 manipulates the grip forceps 48.

Pulleys 99 are attached to drive shafts of the drive motors 95, 96, 97, 98, 100, respectively. The respective drive shafts may be coupled with the respective pulleys 99 through reducers (not shown). The manipulation wires 56, 57, 58, 59, 93 are trained round the respective pulleys 99. The drive motors 95, 96, 97, 98, 100 are individually driven, respectively, and when the pulleys 99 are rotated, the manipulation wires 56, 57, 58, 59, 93 trained around the pulleys 99 are pushed and pulled.

Although the bending portion manipulation mechanism and the surgical portion manipulation mechanism use transmission mechanisms making use of the pulleys 99, they may use, for example, a gear mechanism and the like making use of a pinion gear and a rack. Further, the bending portion manipulation mechanism and the surgical portion manipulation mechanism may use other types of drive actuators in place of the drive motors 95, 96, 97, 98, 100.

As shown in FIGS. 2 and 3, the manipulation unit 41 is connected to the surgical instrument controller 37 through a cable 201. The bending manipulation unit 39 as the manipulation input unit is connected to the surgical instrument controller 37 through a cable 204. In FIG. 3, the surgical instrument controller 37 is provided with a power supply cord 205.

The bending manipulation unit 39 includes a joystick (manipulation input unit) 203 for instructing a position and an attitude of the surgical instrument 40. The joystick 203 includes four joystick switches 203*a*, 203*b*, 203*c*, 203*d* continuously connected in four stages. The joystick switches 203*a*, 203*b*, 203*c*, 203*d* are attached to a manipulation box 210.

When the joystick switches 203*a*, 203*b*, 203*c*, 203*d* are selectively manipulated, the drive motors 95, 96, 97, 98 are individually driven corresponding to the manipulation. With this manipulation, the bending pieces 51, 52, 53, 54 are individually and independently driven in up, down, right, and left directions to thereby bend respective joint portions.

The surgical instrument extreme end movement controller 18 can move the extreme end portion 47 to a desired position by the movement according to the manipulation of the joystick 203. That is, the surgical instrument extreme end movement controller 18 constitutes the surgical instrument 40 which is arranged as a master/slave type and driven electrically. Note that, when the joystick 203 is manipulated by an operator and the like after a control for moving the surgical instrument 40 is set, preference is given to an instruction for manipulating the joystick 203.

As shown in FIG. 2, the surgical instrument controller 37 is provided with a function control input portion 121 for inputting an instruction output from the joystick 203, a condition for controlling the function of the joystick 203, and the like, a motor driver (surgical instrument drive controller) 122 for controlling the drive of the drive motors 95, 96, 97, 98, and a motor unit communication unit 123 connected to the surgical instrument drive unit 38 through the cable 201 for executing communication with the surgical instrument drive unit 38.

The surgical instrument controller 37 transmits a control signal for driving the drive motors 95, 96, 97, 98 in response to the manipulation of the joystick 203 executed by the operator to the motor driver 122 and rotates the drive motors 95, 96, 97, 98. Encoders (not shown) are mounted on the drive motors 95, 96, 97, 98 to measure the number of revolutions thereof. The encoders feedback-control the drive motors 95, 96, 97, 98 by generating signals according to the number of revolutions and transmitting the signals to the motor driver 122.

The relation between a multijointed structure in the bending portion 46 and the joystick 203 will be explained with reference to FIGS. 8A, 8B and 9.

Figure 8A:
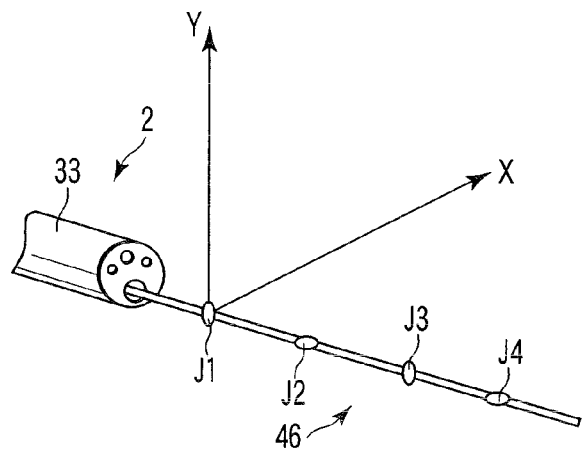
FIG. 8A is an explanatory view of a multijointed structure in the bending portion of a surgical instrument.
Figure 8B:
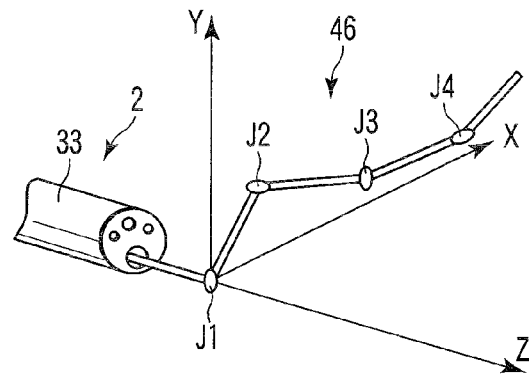
FIG. 8B is an explanatory view of a multijointed structure in the bending portion of the surgical instrument.

As shown in FIG. 8A, in a state that all the joint portions in the bending portion 46 project from the extreme end portion 33, the joints disposed from the manipulation unit side (base end side) to the extreme end side are sequentially referred to as J1, J2, J3, J4. A coordinate system is set using the joint J1 disposed nearest to the manipulation unit side as a reference. In the coordinate system, a Y-axis direction agrees with a vertical direction of the image pickup device. It is assumed that the joints J1, J3 are bent about an X-axis, and the joints J2, J4 are bent about a Y-axis.

Figure 9:
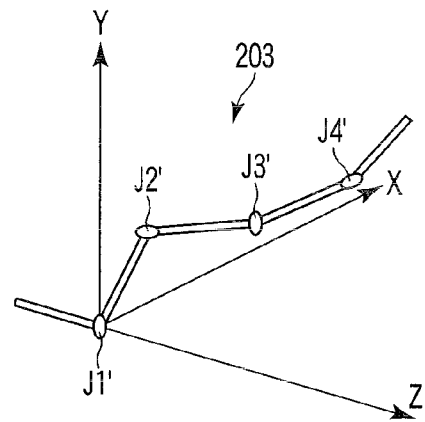
FIG. 9 is an explanatory view of a multijointed structure in a joystick.

As shown in FIG. 9, the joystick 203 (manipulation input unit) includes joints J1', J2', J3', J4' which have the same structures as those of the joint J1 and the joints J2, J3, J4 located nearer to the extreme end side than the joint J1.

The number of the joints and the bending directions of the joystick 203 are the same as those of the bending portion 46. The lengths of respective rods of the joystick 203 are set to values multiplied by an appropriate coefficient k so that the operator can easily manipulate them. When, for example, k=10 and the length of each rod of the surgical instrument 40 is 3 mm, the length of each rod of the joystick 203 (manipulation input unit) is set to 30 mm. Encoders (not shown) are assembled to the joints J1', J2', J3', J4' to measure bent angles. The information of the bent angles measured by the encoders is sent to the surgical instrument controller 37. The surgical instrument controller 37 generates drive signals corresponding to the angle information (the joints J1', J2', J3', J4') and bends the joints J1, J2, J3, J4 by rotating the drive motors 95, 96, 97, 98, respectively. When the joints J1', J2', J3', J4' are bent as shown in, for example, FIG. 9, the joints J1, J2, J3, J4 are bent as shown in FIG. 8B.

Since the bending portion 46 has a the plurality of joints, the extreme end of the surgical instrument 40 can be moved to an arbitrary position and an arbitrary attitude so that an affected area can be more easily cut out and exfoliated than ever before. Further, since the joint structure of the surgical instrument 40 is caused to equally correspond to that of the manipulation input unit, the operator can easily operate the surgical instrument having a plurality of joints.

Further, the drive motor 100 also has a motor driver, a motor unit communication unit, and the like similarly to the drive motors 95, 96, 97, 98. The grip forceps 48 is manipulated by manipulating a manipulation body such as a handle (function control/input unit) 125 disposed in the manipulation unit 41 and the like.

Note that the manipulation input unit may be preferably provided with a first manipulation switch corresponding to the first bending piece 51, a second manipulation switch corresponding to the second bending piece 52, a third manipulation switch corresponding to the third bending piece 53, and a fourth manipulation switch corresponding to the fourth bending piece 54. When, for example, the first manipulation switch is depressed, the first bending piece 51 is bent. Further, the manipulation unit 41 may be preferably provided with a switch device (manipulation switch) for the bending manipulation. The manipulation input unit may use a pen type input unit for inputting a three-dimensional position.

Next, an operation when the surgical instrument 40 is used will be explained.

First, as shown in FIG. 2, the insertion portion 21 is inserted into a body cavity, and the insertion portion 42 is inserted from the insertion port 28 into the insertion channel in this state. The extreme end portion 47 and the bending portion 46 project from the channel port 36 into the body cavity. Then, a work for gripping an affected area and the like in the body cavity is executed using the grip forceps 48 while observing them by the endoscope 2.

In this case, the bending portion 46 can be bent to an appropriate multijointed bent shape according to the state in the body cavity and the surgical procedure. That is, when the joystick 203 is manipulated and the bending pieces 51, 52, 53, 54 are individually rotated, the bending portion 46 is bend into an appropriate shape.

When, for example, the drive motor 95 is driven, the manipulation wires 56a, 56b trained around the pulley 99 in the drive motor 95 are pushed and pulled. With this operation, the first bending piece 51 is independently rotated. When the drive motor 96 is driven, the manipulation wires 57a, 57b trained around the pulley 99 in the drive motor 96 are pushed and pulled. With this operation, the second bending piece 52 is independently rotated. When the drive motor 97 is driven, the manipulation wires 58a, 58b trained around the pulley 99 in the drive motor 97 are pushed and pulled. With this operation, the third bending piece 53 is independently rotated. Further, when the drive motor 98 is driven, the manipulation wires 59a, 59b trained around the pulley 99 in the drive motor 98 are pushed and pulled. With this operation, the fourth bending piece 54 is independently rotated.

Accordingly, the bending pieces 51, 52, 53, 54 are independently rotated by appropriately bending the joystick 203 so that the bending portion 46 is bent. The bending portion 46 is bent even to a complicated shape by adjusting the direction in which the joystick 203 is rotated and the amount of rotation thereof.

As described above, in the embodiment, since the manipulation wires are disposed in the respective bending pieces, it is possible to independently rotate only an arbitrary bending piece. Accordingly, in the embodiment, since the bending mechanism has a plurality of degrees of freedom, a work can be easily executed even in a narrow region such as a body cavity.

In more detail, in the embodiment, since the bending pieces 51, 52, 53, 54 can be independently rotated (bend), the bending portion 46 can be partially bent also in a different direction. Thus, in the embodiment, the bending portion 46 can be bend into an appropriate shape according to a state of use. As a result, since the degree of freedom of bending of the bending portion 46 is increased, it is possible in the embodiment to easily execute even a complex work in a narrow body cavity region as compared with a case in which the bending portion 46 is uniformly bend. Further, in the embodiment, since the attitude of the bending portion 46 can be easily bent so that it does not disturb another surgical instrument or observation with the endoscope 2, the workability of the surgical instrument 40 can be increased.

Since the positions of the guide sheaths are determined in the bending portion 46, the embodiment can prevent the interference between the contained members including the guide sheaths. Further, the manipulation wires inserted into the guide sheaths are prevented from being in direct contact with the other manipulation wires or the contained members thanks to the guide sheaths. As a result, the embodiment can reduce the interference between the manipulation wires and the interference between the manipulation wires and the contained members.

Further, in the embodiment, the manipulation wire connected to the bending piece disposed in the base end side is disposed inwards of the manipulation wire connected to the bending piece disposed in the extreme end side. Accordingly, the embodiment can easily secure the space inwards of the bending piece disposed in the extreme end side. Thus, the embodiment can easily assemble, for example, the surgical function unit (for example, grip forceps 48) and the like to the space.

To explain in detail, the embodiment disposes the manipulation wire for rotating the bending piece disposed in the extreme end side and the guide sheath for guiding the manipulation wire inwards of the manipulation wire for rotating the bending piece disposed in the base end side and the guide sheath for guiding the manipulation wire. With this configuration, the embodiment can easily secure the space S in the central region (inside) in the bending piece disposed in the extreme end side. Accordingly, the embodiment can easily assemble, for example, surgical function parts and the like to the space S.

Since the embodiment compactly disposes the manipulation wire connected to the bending piece disposed in the base end side and the manipulation wire connected to the bending piece disposed in the extreme end side, even if the number of the manipulation wires increases, the embodiment can prevent the manipulation wires from being entangled with each other. Further, since the embodiment can compactly dispose the plurality of the manipulation wires, it can reduce the diameter of the bending mechanism.

To explain in detail, in the embodiment, the manipulation wires 56, 57, 58, 59 can be disposed without being entangled with each other even though they pass through the narrow bending portion 46, and further the manipulation wires 56, 57, 58 can be disposed compactly. In other words, since the embodiment can prevent the manipulation wires 56, 57, 58 from being entangled with each other in the bending portion 46 and reduce occurrence of interference between the manipulation wires, it can smoothly execute a bending manipulation. Further, in the embodiment, since an allowance for disposing other contained member in the bending portion 46 can be made, the diameter of the bending portion 46 can be reduced.

Further, in the embodiment, a guide sheath, which guides a manipulation wire for rotating a bending piece, is connected to a bending piece located just behind the above bending piece (on the base end side). Thus, the embodiment can maximize the efficacy of the wire guide function achieved by the guide sheath. Further, the region in which the manipulation wires are separately exposed can be reduced. Accordingly, the embodiment can avoid any reduction in the wire guide functionality. Further, when, for example, the insertion portion 42 itself is twisted, the embodiment can alleviate the effect of the twist on the wire guide function of the guide sheaths.

Further, in the embodiment, the guide sheaths may be formed of an intimately wound metal coil. With this configuration, the embodiment can sufficiently withstand any abrupt rotating and bending actions of the bending pieces.

Next, a modification of the positioning/disposing mechanism of the embodiment described above will be explained with reference to FIGS. 10A and 10B.

In the modification, no wire guide is used, and guide sheaths are directly positioned and fixed to bending pieces. As shown in, for example, FIG. 10A, holes 124 are formed in the right/left inner wall portions of the second bending piece 52 to flow, for example, a brazing alloy thereinto. The extreme end of the guide sheath 66a is fixed to the right inner wall portion of the second bending piece 52 by the brazing alloy or the like flowed into the hole 124 formed in the right inner wall portion of the second bending piece 52. The extreme end of the guide sheath 66b is fixed to the left inner wall portion of the second bending piece 52 by the brazing alloy or the like flowed into the hole 124 formed in the left inner wall portion of the second bending piece 52. As described above, the second bending piece 52 plays a role as positioning/disposing mechanism for positioning and disposing the manipulation wires 56a, 56b and the guide sheaths 66a, 66b.

Further, as shown in, for example, FIG. 10B, the upper inner wall portion 127a and the lower inner wall portion 127b of the third bending piece 53 are recessed toward the inside of the third bending piece 53. Holes 124 are formed in the upper inner wall portion 127a and the lower inner wall portion 127b. The extreme end of the guide sheath 67a is fixed to the upper inner wall portion 127a by a brazing alloy or the like flowed into the hole 124 formed in the upper inner wall portion 127a. The extreme end of the guide sheath 67b is fixed to the lower inner wall portion 127b by a brazing alloy or the like flowed into the hole 124 formed in the lower inner wall portion 127b. As described above, the third bending piece 53 plays a role as positioning/disposing mechanism for positioning and disposing the manipulation wires 57a, 57b and the guide sheaths 67a, 67b.

As described above, since no wire guide is necessary in the modification, a configuration can be simplified and made small and a manufacturing cost can be reduced.

Figure 12:
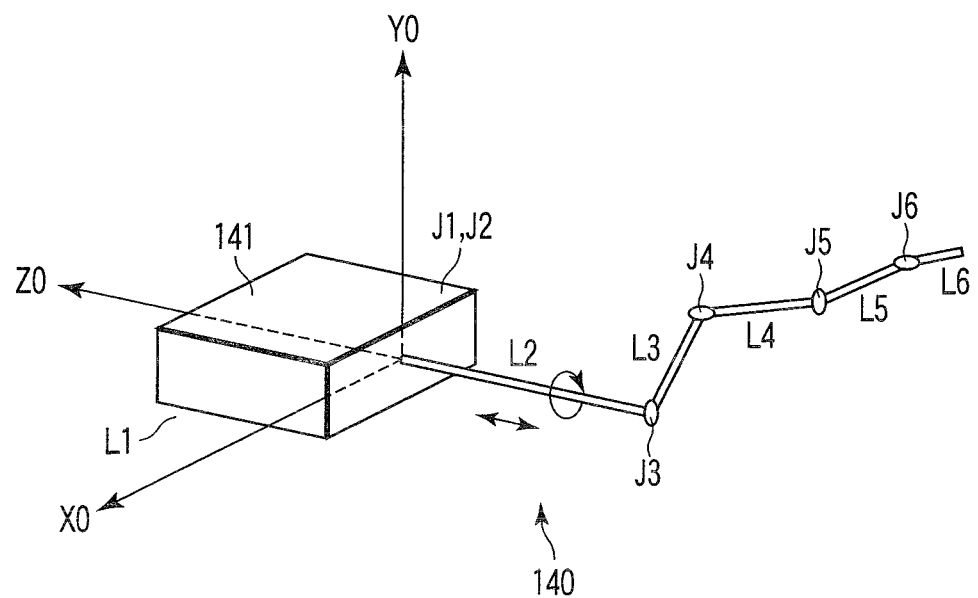
FIG. 12 is an explanatory view of a multijointed structure of a joystick in the embodiment.

Next, another embodiment of the present invention will be explained, with reference to FIGS. 11 and 12. The overall configuration of an endoscope apparatus system in this embodiment is approximately the same as that of the above-described embodiment. However, a motor unit of a surgical instrument 40 is additionally provided with a mechanism 131 for rotating a bending portion 46 around the axis of an insertion portion 42 and a mechanism 132 for advancing the bending portion 46 in the axial direction of the insertion portion 42 in parallel therewith. Further, at least four joints are disposed in the bending portion 46. With this configuration, the position and the attitude of the extreme end portion 47 are arbitrarily controlled. Further, the movement of the surgical instrument 40 corresponds to that of a manipulation input unit 140. A joystick type manipulation input unit having an advancing, retreating, and rotating joint structure is used as the manipulation input unit 140.

A coordinate system is set as shown in FIG. 11. The coordinate system uses a base end portion 141 of the manipulation input unit 140 as a reference and corresponds to the surgical instrument 40. In the coordinate system, the joint J1 moves forward and rearward, the joint J2 rotates in an axial direction, the joints J3, J5 are bent about a Y-axis, and the joints J4, J6 are bent about an X-axis. The rotation angles of the joints J2 to J6 are shown by θ2 to θ6, respectively. The lengths of respective rods are shown by L1 to L5 and the length of an extreme end rod is shown by L6. Thus, conversion matrices in the respective joints J1, J2, J3, J4, J5, J6 are shown by Expression 1 from the kinematics of the manipulator (surgical instrument 40).

[Expression 1]

$$Joint J1: T_0^1 = \begin{pmatrix} 1 & 0 & 0 & 0 \\ 0 & 1 & 0 & 0 \\ 0 & 0 & 1 & -L_1 \\ 0 & 0 & 0 & 1 \end{pmatrix}$$

$$Joint J2: T_1^2 = \begin{pmatrix} \cos\theta_2 & -\sin\theta_2 & 0 & 0 \\ \sin\theta_2 & \cos\theta_2 & 0 & 0 \\ 0 & 0 & 1 & -L_2 \\ 0 & 0 & 0 & 1 \end{pmatrix}$$

$$Joint J3: T_2^3 = \begin{pmatrix} \cos\theta_3 & 0 & \sin\theta_3 & -L_3\sin\theta_3 \\ 0 & 1 & 0 & 0 \\ -\sin\theta_3 & 0 & \cos\theta_3 & -L_3\cos\theta_3 \\ 0 & 0 & 0 & 1 \end{pmatrix}$$

-continued $$\text{Joint } J4: T_3^4 = \begin{pmatrix} 1 & 0 & 0 & 0 \\ 0 & \cos\theta_4 & -\sin\theta_4 & L_4\sin\theta_4 \\ 0 & \sin\theta_4 & \cos\theta_4 & -L_4\cos\theta_4 \\ 0 & 0 & 0 & 1 \end{pmatrix}$$

$$\text{Joint } J5: T_4^5 = \begin{pmatrix} \cos\theta_5 & 0 & \sin\theta_5 & -L_5\sin\theta_5 \\ 0 & 1 & 0 & 0 \\ -\sin\theta_5 & 0 & \cos\theta_5 & -L_5\cos\theta_5 \\ 0 & 0 & 0 & 1 \end{pmatrix}$$

$$\text{Joint } J6: T_5^6 = \begin{pmatrix} 1 & 0 & 0 & 0 \\ 0 & \cos\theta_6 & -\sin\theta_6 & L_6\sin\theta_6 \\ 0 & \sin\theta_6 & \cos\theta_6 & -L_6\cos\theta_6 \\ 0 & 0 & 0 & 1 \end{pmatrix}$$

Accordingly, a homogeneous conversion matrix is shown by Expression 2.

$$T_0^6 = T_0^1 T_1^2 T_2^3 T_3^4 T_4^5 T_5^6 \quad \text{[Expression 2]}$$

$$= \begin{pmatrix} r_{11} & r_{12} & r_{13} & t_x \\ r_{21} & r_{22} & r_{23} & t_y \\ r_{31} & r_{32} & r_{33} & t_z \\ 0 & 0 & 0 & 1 \end{pmatrix}$$

Since the coordinate system uses the base end portion 141 as the reference, the position (x, y, z) and the attitude ($\theta x$, $\theta y$, $\theta z$) of the extreme end portion of the manipulation input unit 140 are determined by Expression 3.

$$\begin{pmatrix} x \\ y \\ z \end{pmatrix}^T = \begin{pmatrix} t_x \\ t_y \\ t_z \end{pmatrix}^T \quad \text{[Expression 3]}$$

$$\begin{pmatrix} \theta_x \\ \theta_y \\ \theta_z \end{pmatrix}^T = \begin{pmatrix} a\sin(r_{32}/\cos\theta_y) \\ a\sin(-r_{31}) \\ a\sin(r_{21}/\cos\theta_y) \end{pmatrix}^T$$

The configuration of the surgical instrument 40 is different from that of the manipulation input unit 140. Accordingly, to operate the surgical instrument 40 by operating the manipulation input unit 140, it is necessary to match the position and the attitude of the surgical instrument 40 with those of the manipulation input unit 140. For this purpose, the rotation angles and the amounts of parallel (forward and rearward) movement of the respective joints of the surgical instrument 40 must be determined.

As described above, the movement of the surgical instrument 40 corresponds to that of the manipulation input unit 140. Accordingly, the position and the attitude of the surgical instrument 40 are determined by those of the manipulation input unit 140. Assuming that the configuration of the surgical instrument 40 is known, the rotation angles and the amounts of parallel movement of the respective configurations of the surgical instrument 40 can be determined by inverse kinematics. Inverse kinematics is a method of estimating the specific values of the joints (angles and the like thereof) from the position/attitude information of the manipulator (surgical instrument 40) in a working space. The joint parameter $\Phi$ of the respective joints 1, 2, ..., n are shown by Expression 4.

$$\Phi = (\theta_1, \theta_2, \ldots, \theta_n)^T \quad \text{[Expression 4]}$$

The position and the attitude of the manipulator are shown by Expression 5.

$$E_p = (x_{Ep}, y_{Ep}, z_{Ep}, \text{Roll}_{Ep}, \text{Yaw}_{Ep}, \text{Pitch}_{Ep})^T \quad \text{[Expression 5]}$$

Thus, the relation thereof is shown by Expression 6.

$$E_p = A(\Phi) \quad \text{[Expression 6]}$$

Here, the target P of the position and the attitude of the manipulator is shown by Expression 7.

$$P_p = (x_{Pp}, y_{Pp}, z_{Pp}, \text{Roll}_{Pp}, \text{Yaw}_{Pp}, \text{Pitch}_{Pp})^T \quad \text{[Expression 7]}$$

To place the manipulator in a $P_p$ state, $\Phi$ must be determined to satisfy Expression 8.

$$P_p = A(\Phi) \quad \text{[Expression 8]}$$

However, since these expressions are non-linear, ordinarily, Jacobian matrix $J(\Phi)$ is determined by subjecting Ep to partial differentiation by the factor of $\Phi$ to determine $\Phi$.

$$J(\Phi) = \begin{pmatrix} \frac{dx_{ep}}{d\theta_1} & \frac{dx_{ep}}{d\theta_2} & \cdots & \frac{dx_{ep}}{d\theta_n} \\ \frac{dy_{ep}}{d\theta_1} & \frac{dy_{ep}}{d\theta_2} & \cdots & \frac{dy_{ep}}{d\theta_n} \\ \frac{dz_{ep}}{d\theta_1} & \frac{dz_{ep}}{d\theta_2} & \cdots & \frac{dz_{ep}}{d\theta_n} \\ \frac{d\text{Roll}_{ep}}{d\theta_1} & \frac{d\text{Roll}_{ep}}{d\theta_2} & \cdots & \frac{d\text{Roll}_{ep}}{d\theta_n} \\ \frac{d\text{Yaw}_{ep}}{d\theta_1} & \frac{d\text{Yaw}_{ep}}{d\theta_2} & \cdots & \frac{d\text{Yaw}_{ep}}{d\theta_n} \\ \frac{d\text{Pitch}_{ep}}{d\theta_1} & \frac{d\text{Pitch}_{ep}}{d\theta_2} & \cdots & \frac{d\text{Pitch}_{ep}}{d\theta_n} \end{pmatrix} \quad \text{[Expression 9]}$$

Expression 11 is determined from Expression 10.

$$\dot{\Phi} = J(\Phi)^{-1} \dot{E}_p \quad \text{[Expression 10]}$$

$$P_p = A(\Phi) \quad \text{[Expression 11]}$$

Then, $\Phi$ that satisfies Expression 11 is determined by a convergence calculation.

As a result, according to the embodiment, even when the configuration of the manipulation input unit 140 is different from that of the surgical instrument 40, the extreme end of the surgical instrument 40 can be moved to an arbitrary position and an arbitrary attitude from the position and the attitude of the manipulation input unit 140, and an affected area can be cut out and exfoliated more easily than ever before.

The present invention can be also applied to a bending portion of an endoscope. The present invention can be applied to, for example, the bending mechanism of the bending portion in the insertion portion of the endoscope according to the embodiment described above. Further, the surgical instrument as a target of the present invention also includes a surgical catheter.

Note that, in the explanation of the embodiment described above, the numerals of the bending pieces, the manipulation wires, the guide sheaths, and the wire guides are used to explain the embodiment and do not always agree with the numerals described in the claims. For example, there are cases where a first bending piece in the claim is the second bending piece in the embodiment, and a second bending piece in the claim is the third bending piece in the embodiment.

<Additional Statement>

According to the above explanation, there can be obtained multijointed medical equipment according to the following items or arbitrary combinations of the following items and the items according to the claims.

1. An endoscope surgical instrument including:
   an endoscope to observe an affected area in a body cavity;
   a surgical instrument to perform surgery on the affected area by passing through an insertion portion of the endoscope;
   at least one bending mechanism disposed in an extreme end of the surgical instrument;
   manipulation mechanism for moving the extreme end of the surgical instrument in a direction intended by an operator;
   control mechanism for controlling movement of the extreme end of the surgical instrument in response to manipulation of the manipulation mechanism; and
   mechanism for operating the bending mechanism of the surgical instrument in response to a control signal from the control mechanism.

2. The endoscope surgical instrument according to item 1, wherein the surgical instrument includes a soft insertion portion and a surgical portion for cutting out and exfoliating an affected area of a living body.

3. The endoscope surgical instrument according to item 1, wherein power for operating the bending mechanism is assembled in the vicinity of the extreme end of the surgical instrument.

4. The endoscope surgical instrument according to item 1, in which power for operating the bending mechanism is disposed in a portion other than the vicinity of the extreme end of the surgical instrument and which includes transmission mechanism for transmitting the power to the bending mechanism.

5. The endoscope surgical instrument according to item 1, including mechanism for moving the extreme end of the surgical instrument forward and rearward.

What is claimed is:

1. A multijointed bending mechanism comprising:
   a first bending piece;
   a second bending piece connected to the first bending piece so as to be rotatable around a first rotation shaft and provided closer to a base end side of the multijointed bending mechanism than the first bending piece;
   a third bending piece connected to the second bending piece so as to be rotatable around a second rotation shaft and provided closer to a base end side of the multijointed bending mechanism than the second bending piece;
   at least two first wires connected to the first bending piece to rotate the first bending piece and inserted into the third bending piece;
   at least two second wires connected to the second bending piece to rotate the second bending piece and inserted into the third bending piece; and
   a positioning/disposing mechanism configured to execute positioning so that the second wires which are inserted into the third bending piece are disposed closer to a center axis side of the multijointed bending mechanism than the first wires which are inserted into the third bending piece.

2. The multijointed bending mechanism according to claim 1, further comprising positioning/disposing mechanism disposed in the second bending piece for executing positioning so that the second wires are disposed inwards of the first wires.

3. The multijointed bending mechanism according to claim 1, further comprising:
   a first elastic member connected to the second bending piece to guide the first wires; and
   a second elastic member connected to the third bending piece to guide the second wires.

4. The multijointed bending mechanism according to claim 3, wherein the positioning/disposing mechanism is disposed in the third bending piece.

5. A multijointed medical equipment comprising the multijointed bending mechanism according to claim 1.

6. A multijointed bending mechanism comprising:
   a first bending piece;
   a second bending piece connected to the first bending piece so as to be rotatable around a first rotation shaft and provided closer to a base end side of the multijointed bending mechanism than the first bending piece;
   a third bending piece connected to the second bending piece so as to be rotatable around a second rotation shaft and provided closer to a base end side of the multijointed bending mechanism than the second bending piece;
   a fourth bending piece connected to the third bending piece so as to be rotatable around a third rotation shaft and provided closer to a base end side of the multijointed bending mechanism than the third bending piece;
   at least two first wires connected to the first bending piece to rotate the first bending piece and inserted into the fourth bending piece;
   at least two third wires connected to the third bending piece to rotate the third bending piece and inserted into the fourth bending piece; and
   a positioning/disposing mechanism configured to execute positioning so that the third wires which are inserted into the fourth bending piece are disposed closer to a center axis side of the multijointed bending mechanism than the first wires which are inserted into the fourth bending piece.

7. The multijointed bending mechanism according to claim 6, wherein the positioning/disposing mechanism is disposed in the fourth bending piece.

8. The multijointed bending mechanism according to claim 6, further comprising:
   a first elastic member connected to the second bending piece to guide the first wires; and
   a third elastic member connected to a fourth bending piece rotatably connected to the third bending piece to guide the third wires.

9. The multijointed bending mechanism according to claim 8, further comprising positioning/disposing mechanism disposed in the third bending piece for executing positioning so that the third wires are disposed inwards of the first wires.

10. A multijointed medical equipment comprising the multijointed bending mechanism according to claim 6.

11. The multijointed bending mechanism according to claim 1, wherein the positioning/disposing mechanism comprises cut and raised pieces formed of a part of a peripheral surface of the second bending piece recessed to inside thereof.

12. The multijointed bending mechanism according to claim 1, wherein:
   the second bending piece comprises right and left inner wall portions,
   the third bending piece comprises upper and lower inner wall portions recessed to inside thereof,
   the positioning/disposing mechanism comprises a first guide sheath configured to guide the first wires and a second guide sheath configured to guide the second wires, and
   the first guide sheath is fixed to the right and left inner wall portions and the second guide sheath is fixed to the upper and lower inner wall portions.

13. The mulitjointed bending mechanism according to claim 6, wherein the positioning/disposing mechanism comprises first cut and raised pieces formed of a part of a peripheral surface of the fourth bending piece recessed to inside thereof and a first guide sheath which the third wires inserted into and is fixed the first cut and raised pieces.

14. The multijointed bending mechanism according to claim 13, wherein:
- the positioning/disposing mechanism further comprises second cut and raised pieces formed of a part of a peripheral surface of the third bending piece recessed to inside thereof and a second guide sheath which the first wires inserted into and is inserted into space portion formed at second cut and raised pieces,
- the second guide sheath is inserted into the fourth bending piece, and
- the first guide sheath is disposed closer to a center axis side of the multijointed bending mechanism than the second guide sheath.

* * * * *